United States Patent [19]

Iizuka et al.

[11] Patent Number: 4,857,650

[45] Date of Patent: * Aug. 15, 1989

[54] NOVEL RENIN INHIBITORY AMINO ACID DERIVATIVES

[75] Inventors: Kinji Iizuka; Tetsuhide Kamijo; Tetsuhiro Kubota, all of Nagano; Kenji Akahane, Tokyo; Hideaki Umeyama, Chiba; Yoshiaki Kiso, Osaka, all of Japan

[73] Assignee: Kissei Pharmaceutical Co., Ltd., Nagano, Japan

[*] Notice: The portion of the term of this patent subsequent to Apr. 7, 2004 has been disclaimed.

[21] Appl. No.: 879,741

[22] Filed: Jun. 27, 1986

[30] Foreign Application Priority Data

Jun. 28, 1985 [JP] Japan .................................. 60-143593
Aug. 5, 1985 [JP] Japan .................................. 60-171975
Nov. 20, 1985 [JP] Japan .................................. 60-260904

[51] Int. Cl.$^4$ ........................................... C07D 233/64
[52] U.S. Cl. ..................................... 548/336; 548/344
[58] Field of Search ............................... 548/344, 336

[56] References Cited

U.S. PATENT DOCUMENTS

| | | | |
|---|---|---|---|
| 3,280,098 | 10/1966 | Otsuka et al. ............... | 548/336 X |
| 4,234,571 | 11/1980 | Nestor et al. ................. | 424/177 |
| 4,548,926 | 10/1985 | Matsueda et al. ............ | 514/19 |
| 4,591,648 | 5/1986 | Jones et al. ................... | 548/344 |
| 4,595,677 | 6/1986 | Riniker et al. ................ | 514/17 |
| 4,656,269 | 4/1987 | Iizuka et al. .................. | 548/344 X |
| 4,666,888 | 5/1987 | Raddatz et al. ............... | 514/18 |
| 4,698,329 | 5/1987 | Matsueda et al. ............ | 514/18 |
| 4,711,958 | 12/1987 | Iizuka et al. . | |

FOREIGN PATENT DOCUMENTS

| | | |
|---|---|---|
| 77028 | 4/1983 | European Pat. Off. . |
| 77029 | 4/1983 | European Pat. Off. . |
| 81783 | 6/1983 | European Pat. Off. . |
| 114993 | 8/1984 | European Pat. Off. . |
| 0173481 | 3/1986 | European Pat. Off. . |
| 0229667 | 7/1987 | European Pat. Off. . |
| 58-39149 | 7/1983 | Japan . |
| 103230 | 12/1984 | Japan . |
| 19100 | 8/1985 | Japan . |
| 201036 | 4/1986 | Japan . |
| 273913 | 7/1986 | Japan . |
| 13908 | 10/1986 | Japan . |
| 265921 | 12/1986 | Japan . |
| 267947 | 12/1986 | Japan . |
| 285317 | 12/1986 | Japan . |
| 268415 | 6/1987 | Japan . |

OTHER PUBLICATIONS

Kobuku et al., "Highly Potent and Specific Inhibitors, Etc.," Biochemical and Biophysical Research Comm., vol. 118, No. 3, pp. 929-933 (2-1984).
106th Annual Meeting of Pharmaceutical Society of Japan (Apr. 1986)–Iizuka et al. presentation.
The 50th Annual Meeting of the Japanese Circulation Society (Mar. 1986)–Aoi et al., abstract followed by presentation.
50th Annual Meeting of the Japanese Circulation Society (Mar. 1986) Miyazaki et al. abstr.
59th General Meeting of the Japanese Pharmacological Society (Apr. 1986) Miyazaki et al. abstr. & presentation.
Brown et al., "Protection of Histidine Side-Chains, etc.", Chemical Abstracts 95:220299f (1981).
Colombo et al., "Acid-Labile Histidine Side-Chain Protection," Chemical Abstracts 101:23914n (1984).
Matsueda et al, "Short Chain Peptide Inhibitors of Human Renin", Chemistry Letters, Chem. Soc. Japan, No. 7, pp. 1041-1044 (1985).
Patent Abstracts of Japan, unexamined applications, C Section, vol. 2, No. 43, Mar. 23, 1978, p. 4928.

*Primary Examiner*—Joseph Paul Brust
*Attorney, Agent, or Firm*—Sughrue, Mion, Zinn, Macpeak & Seas

[57] ABSTRACT

New renin inhibitory amino acid derivatives represented by formula (I):

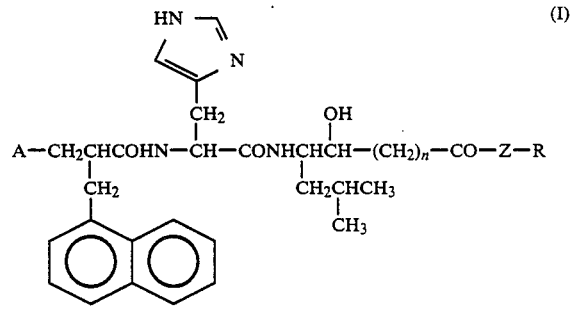

wherein A represents an alkoxycarbonyl group having 2 to 7 carbon atoms,

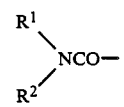

wherein $R^1$ and $R^2$ are defined as in the specification below or

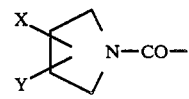

wherein X and Y are defined as in the specification herein below, n represents zero or one, Z represents —O— or —NH—, and R represents a straight- or branched chain alkyl group having 1 to 7 carbon atoms, and pharmaceutically acceptable salts thereof, useful as a therapeutic agent are disclosed. The amino acid derivatives have a renin inhibitory effect when administered orally and are useful for treatment of hypertension, especially renin-associated hypertension.

32 Claims, No Drawings

NOVEL RENIN INHIBITORY AMINO ACID DERIVATIVES

FIELD OF THE INVENTION

This invention relates to novel amino acid derivatives useful as a therapeutic agent. More particularly, this invention relates to amino acid derivatives which have a human renin inhibitory effect when administered orally, and thus which are useful for treatment of hypertension, especially renin-associated hypertension.

BACKGROUND OF THE INVENTION

Renin is a proteolytic enzyme having a molecular weight of about 40,000, produced and secreted by juxtaglomerular cells in the kidney. This acts on the plasma renin substrate, angiotensinogen, to yield decapeptide angiotensin I which is converted into angiotensin II by an angiotensin I converting enzyme.

It is well known that angiotensin II contacts the vascular smooth muscle and acts on the adrenal cortex to secrete the aldosterone which regulates salts and water balance. Accordingly, the renin-angiotensin system plays an important role in hypertension. In fact, a specific inhibitor of angiotensin I converting enzyme has been investigated and developed as a practical medicament for hypertension. Thus, an effective inhibitor of renin has long been sought as an agent for treatment of hypertension, especially renin-associated hypertension. As a result, it has been found that certain peptides show a renin inhibitory effect, as described in Japanese Patent Application (OPI) Nos. 155345/84, 227851/84 and 110661/84, (The term "OPI" as used herein refers to an unexamined Japanese patent application); Japanese Patent Publication No. 39149/83, Biochemical and Biophysical Research Communications, Vol. 118, pages 929-933, 1984; and European Patent Application Nos. 77029(A2), 77028(A2) and 81783(A2).

Of these prior art references, Japanese Patent Application (OPI) No. 155345/84 discloses peptides represented by the following formula:

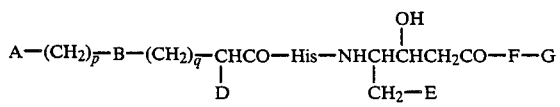

wherein A represents a hydrogen atom, a phenyl group or 10,11-dihydro-5H-dibenzo[a,d]cycloheptenyl group, B represents —O—, —CH=CH— or —CH$_2$—, p and q may be the same or different and each represents an integer of from 0 to 3, D represents a hydrogen atom, a lower alkyl group, a lower alkenyl group, a phenyl group or a phenylalkyl group, E represents a phenyl group, a cyclohexyl group or an isopropyl group, His represents an L-histidyl group, F represents a residual group of an amino acid such as an L-leucyl, an L-isoleucyl, an L-leucyl-L-phenylalanyl, an L-phenylalanyl-L-phenylalanyl and an L-alanyl-L-phenylalanyl group, and G represents a protective group attached to the terminal carbon atom of an amino acid, such as an amino group, an alkylamino group, an arylalkylamino group and an alkoxy group.

Japanese Patent Application (OPI) No. 227851/84 also discloses peptides represented by the following formula:

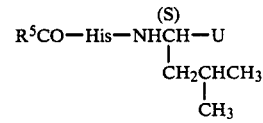

wherein R$^5$CO— represents an aliphatic acyl group, an aromatic acyl group, an aromatic aliphatic acyl group, a heterocyclic acyl group or a heterocyclic aliphatic acyl group, said acyl groups may be substituted with an amino, a protected amino, a hydroxy, a substituted dithio, an alkyl, an alkoxy, an alkoxycarbonyl, or a nitro group or a halogen atom; U represents a formyl group, or

wherein R$^6$ represents a hydrogen atom, an alkyl group, or an alkyl group having a hydroxy, a mercapto, an amino, a carbamoyl, a formyl, an aromatic ring or a heterocyclic ring substituent; Z represents a hydroxy, a mercapto or a formyl group, or U represents

wherein R$^7$ represents a hydroxy group or an alkyl group having a hydroxy, a mercapto, an amino, a carbamoyl, or a formyl group, or an aromatic ring or a heterocyclic ring substituent; His represents an L-histidyl group;

represents a carbon atom in the S-configuration, provided that, when U represents a formyl group, R$^5$CO— does not represent a benzyloxycarbonyl-L-phenylalanyl group or a benzyloxycarbonyl-L-prolyl-L-phenylalanyl group.

The noted Biochemical and Biophysical Research Communications article discloses a peptide represented by the formula:

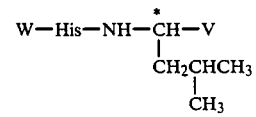

wherein W represents a benzyloxycarbonyl group, an N-benzyloxycarbonyl-L-phenylalanyl group or an N-benzyloxycarbonyl-3-(1-naphthyl)-L-alanyl group, V represents a formyl group or a hydroxymethyl group and C represents a carbon atom in the L-configuration.

Japanese Patent Publication No. 39149/83 discloses peptides represented by the following formula:

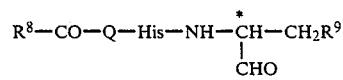

wherein R[8] represents a methyl group, an ethyl group, a benzyl group, an adamantyl group or a benzyloxy group, Q represents an L-phenylalanyl group, an L-prolyl-L-phenylalanyl group or an L-histidyl-L-prolyl-L-phenylalanyl group, His represents an L-histidyl group, R[9] represents an isopropyl group, and C represents a carbon atom in the L-configuration. These peptides show a renin inhibitory effect, however, they are easily hydrolyzed by proteolytic enzymes of the gastorointestinal tract such as chymotrypsins. Therefore, these peptides have drawback that their renin inhibitory effect can not be expected when they are administered orally.

On the other hand, the peptides disclosed in the above European Patent Applications are polypeptides and have difficulties in their preparation and purification. Furthermore, they lose their pharmacological effects when administered orally similar to the peptides disclosed in the Japanese Patent Publication No. 39149/83, and their utility is thus limited.

Furthermore, the following peptide compounds were reported to have a human renin inhibitory activity in 106th Annual Meeting of the Pharmaceutical Society of Japan. (April, 1986) and The Meeting of Japanese Circulation Journal (March, 1986), respectively:

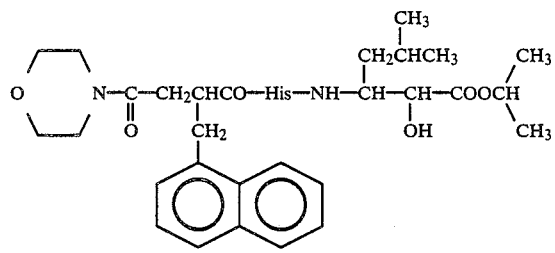

wherein His represents L-histidyl group.

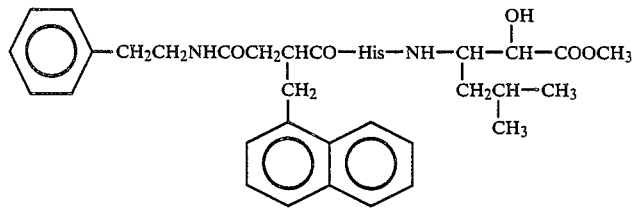

wherein His represents L-histidyl group.

Thus, development of renin inhibitors which can display a sufficient therapeutic effect by oral administration has long been desired.

SUMMARY OF THE INVENTION

Accordingly, an object of this invention is to provide new amino acid derivatives which exhibit a specific renin inhibitory effect when administered orally to mammalia including humans.

Another object of this invention is to provide new amino acid derivatives and pharmaceutically acceptable salts thereof.

A further object of this invention is to provide pharmaceutical compositions comprising dipeptides or pharmaceutically acceptable salts thereof.

A still further object of this invention is to provide methods for the treatment of hypertension using new amino acid derivatives or pharmaceutically acceptable salts thereof.

Other objects, features and advantages of this invention will be apparent from the following description of the invention.

The present invention provides new amino acid derivatives represented by formula (I):

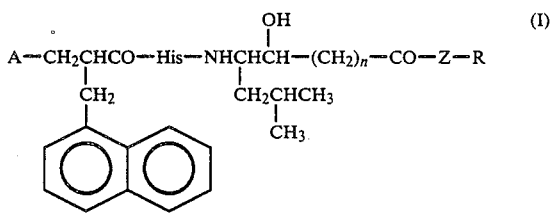

wherein A represents an alkoxycarbonyl group having 1 to 7 carbon atoms,

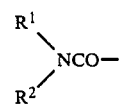

wherein $R^1$ represents hydrogen atom, an alkyl group having 1 to 6 carbon atoms or a hydroxy alkyl group and $R^2$ represents hydrogen atom or a straight- or branched-chain alkyl group having 1 to 4 carbon atoms with one or two substituents selected from a hydroxy group, an alkoxycarbonyl group having 2 to 7 carbon atoms, carbamoyl group and an N-substituted carbamoyl group or

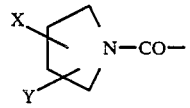

wherein X represents an alkoxycarbonyl group or a hydroxymethyl group; Y represents a hydrogen atom or a hydroxy group; His represents L-histidyl group, n represents zero or one; Z represents —O— or —NH—, and R represents a straight- or branched-chain alkyl group having 1 to 7 carbon atoms, and a pharmaceutically acceptable acid addition salts thereof.

DETAILED DESCRIPTION OF THE INVENTION

These amino acid derivatives of formula (I) of the present invention and pharmaceutically acceptable salts thereof inhibit renin activity in a human renin-sheep renin substrate system. Furthermore the amino acid derivatives of the present invention are stable against proteolytic enzymes such as pepsin and chymotrypsins.

These findings demonstrate that the amino acid derivatives of formula (I) of the present invention exhibit a human renin inhibitory effect when administered orally to mammalia, including humans, and thus are useful for treatment of hypertension, especially renin-associated hypertension.

The amino acid derivatives of formula (I) of the present invention can be prepared according to well known method. That is, the amino acid derivatives of the present invention represented by formula (I):

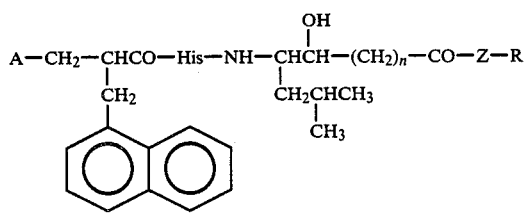

wherein A, His, n, Z and R have the same meanings as defined above, can be prepared by reacting a compound represented by formula (II):

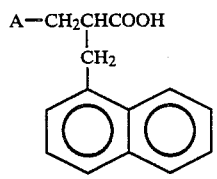

wherein A has the same meaning as defined above, with a compound represented by formula (III):

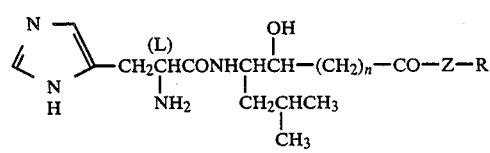

wherein n, Z and R have the same meanings as defined above, $$\overset{(L)}{C}$$

means a carbon atom in the L-configuration.

The compounds of formula (II) used as starting materials can be prepared by a method described in literature or an analogous method these of. For example, the acid compounds represented by formula (II) can be prepared by reacting 1-naphthaldehyde with diethyl succinate to obtain the compound represented by formula (IV):

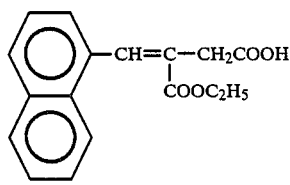

hydrolyzing the resulting compound to obtain the corresponding dicarboxylic acid, dehydrating the dicarboxylic acid compound obtained in acetic anhydride to obtain an succinic anhydride compound represented by formula (V):

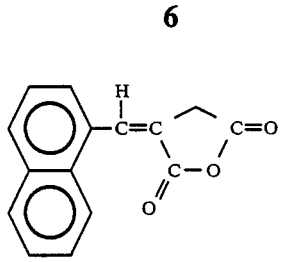

reacting the succinic anhydride compound with an amine, ammonia or alcohol to obtain a compound represented by formula (VI):

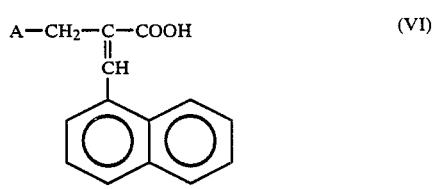

wherein A has the same meaning as defined above, and then hydrogenating the resulting compound over palladium charcoal.

The compounds represented by formula (III) used as starting materials can be prepared by reacting N-protected L-histidine methyl ester with hydrazine in methanol to obtain a compound represented by the formula (VII):

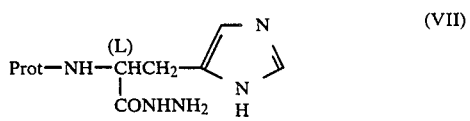

wherein $$\overset{(L)}{C}$$

has the same meaning as defined above, Prot means a protective group of amino group, reacting the obtained compound with isoamyl nitrite, and reacting the resultant compound with a compound represented by formula (VIII):

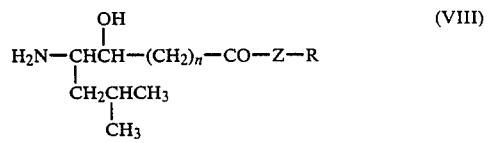

wherein n, Z* and R have the same meanings as defined above, and then removing the protective group from the amino group.

The compound of formula (VIII) can be prepared by a method described in literature or an analogous method thereof. That is, the compound wherein n is 0 can be prepared by esterifing or amidating 3-amino-2-hydroxy-5-methylhexanoic acid which is prepared according to the method described in J. Org. Chem., Vol. 45, pages 2288–2290, 1980. The compound wherein n is 1 can be prepared by esterifing or amidating statine or N-(tert-butyloxycarbinyl)statine.

The reaction of a compound represented by formula (II) with a compound of formula (III) can be carried out according to the following manner.

That is, the amino acid derivative of formula (I) of the present invention can be prepared by dissolving compounds of formulae (II) and (III) in N,N-dimethylformamide, adding successively diphenyl phosphoryl azide and triethylamine to the solution with stirring under ice-cooling, and stirring the mixture overnight, and then treating the reaction mixture according to usual manner.

The amino acid derivatives represented by formula (I) of the present invention can be converted according to conventional method to a pharmaceutically acceptable salt thereof. Examples of such pharmaceutically acceptable salts include pharmaceutically acceptable inorganic or organic acid salts such as a hydrochloric acid salt, a sulfuric acid salt, a p-toluenesulfonic acid salt, an acetic acid salt, a citric acid salt, tartaric acid salt, a succinic acid salt, a fumaric acid salt and the like. These salts have a renin inhibitory effect as high as the corresponding compound having a free amino group and are stable against proteolytic enzyme, and thus they show the desired renin inhibitory effect even by oral administration.

The amino acid derivatives represented by formula (I) of the present invention possess a strong inhibitory effect on human renin, for example, the amino acid derivatives of formula (I) produce a 50% inhibition in a human renin-sheep renin substrate system and in a human high renin plasma at $10^{-7}$ to $10^{-8}$ and $10^{31\ 6}$ to $10^{-9}$ molar concentrations, respectively, and reduce blood pressure of marmoset in a high renin state with a low toxicity, and thus are useful as a therapeutically active agent for treatment of hypertension, especially renin-associated hypertension.

The amino acid derivatives represented by formula (I) and the pharmaceutically acceptable salts thereof of this invention have four or five asymmetric carbons and thus there are several steric isomers. In this invention, those isomers or a mixture thereof can be employed.

The amino acid derivatives represented by formula (I) and the pharmaceutically acceptable salts thereof of this invention can be administered to mammalia, including humans, by oral, intravenous, intramuscular, or intrarectal administration, and for administration they can be formulated into pharmaceutical compositions together with conventional pharmaceutically acceptable carriers or excipients.

The amino acid derivatives and the pharmaceutically acceptable salts of the formula (I) of the present invention can be administered in various dosage forms depending upon the intended therapy. Typical dosage forms which can be used are tablets, pills, powders, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated into sugar-coated tablets, gelatin-coated tablets, film-coated tablets, or tablets coated with two or more layers.

When the pharmaceutical composition is formulated into an injectable preparation, it is preferred that the resulting injectable solution and suspension are sterilized and rendered isotonic with respect to blood. In making the pharmaceutical composition in a form of solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of the amino acid derivatives of the present invention may be in a range of from about 5 mg to 5,000 mg per adult human by oral administration per day, or from about 1 mg to 1,000 mg per adult human by parenteral administration per day in multiple doses depending upon the type of disease, the severity of condition to be treated, and the like.

This invention is further illustrated in more detail by way of the following examples and reference examples. The melting point of the product obtained was uncorrected. The NMR spectra of the products were measured by JEOL's High Resolution NMR Spectrometer Type JNM-GX 270. The Mass spectra of the products were measured by JEOL's Mass Spectrometer Type JMS-DX 300 according to the FAB method. Thin layer chromatography was carried out using Merck's precoated plates silica-gel 60 $F_{254}$ and column chromatography was carried out by employing Merck's Kiesel gel 60 (230–440 mesh). Thin layer chromatography was carried out by using a lower layer of a mixture of chloroform, methanol and water in a proportion of 8/3/1 (by volume) (mixture A) and a mixture of chloroform and methanol in a proportion of 5/1 (by volume) (mixture B) as eluents, and an $Rf_1$ (mixture A) value and $Rf_2$ (mixture B) value were calculated.

Reference Example 1

2-(1-Naphthylmethyl)-3-(2S-methoxycarbonylpyrrolidinocarbonyl)propionic acid

To a solution of 32.3 g of ethyl succinate and 29.0 g of 1-naphthaldehyde in 320 ml of absolute ethyl alcohol was added 10.7 g of a 50% sodium hydride (dispersion in mineral oil) with stirring under ice-cooling, and then the mixture was reflux for 0.5 hours. To the reaction mixture was added 230 ml of a 1N-aqueous sodium hydroxide solution, and the mixture was reflux for 1 hour. The reaction mixture was concentrated under reduced pressure, and water was added to the residue. The mixture was extracted with diethyl ether to remove neutral substances. An aqueous layer was acidified by the addition of concentrated hydrochloric acid, and the acid solution was extracted with diethyl ether. The ethereal layer was washed with a saturated sodium chloride aqueous solution, dried over magnesium sulfate and concentrated under reduced pressure. Benzene was added to the residue, and precipitated crystals were collected by filtration to obtain 26.5 g of 2-(1-naphthylmethylene)succinic acid as yellow crystals.

A mixture of 24.5 g of the 2-(1-naphthylmethylene)-succinic acid in 260 ml of acetic anhydride was heated at 60° C. for 1 hour. The reaction mixture was concentrated under reduced pressure, and a mixture of benzene and hexane (1:1 by volume) was added to the residue.

Precipitated crystals were collected by filtration to obtain 16.0 g of 2-(1-naphthylmethylene)succinic anhydride as orange yellow crystals.

To a solution of 348 mg of L-proline methyl ester hydrochloride in 15 ml of dichloromethane were added 0.29 ml of triethylamine and 500 mg of 2-(1-naphthylmethylene)succinic anhydride, and the mixture was stirred at room temperature for 2 hours. The reaction mixture was washed successively with diluted hydrochloric acid and a saturated sodium chloride aqueous solution, dried over magnesium sulfate, and concentrated under reduced pressure. The residue was purified with silica gel flash column chromatography (eluent: chloroform/methanol=15/1 by volume) to obtain 661 mg of 2-(1-naphthylmethylene)-3-(2S-methoxycarbonylpyrrolidinocarbonyl)propionic acid.

A solution of 600 mg of the propionic acid compound in 25 ml of methanol was hydrogenated over 120 mg of a 10% palladium charcoal under a hydrogen atmosphere at room temperature. After filtration of the reaction mixture, the filtrate was concentrated under reduced pressure to obtain 543 mg of 2-(1-naphthylmethyl)-3-(2S-methoxycarbonylpyrrolidinocarbonyl)propionic acid as white crystals.

$Rf_1$: 0.65.
Melting point: 77°–83° C.
IR (KBr): $\nu$co 1740, 1640 cm$^{-1}$.

Reference Example 2

The following acid compounds were prepared in an analogous manner to that described in Reference Example 1.

2-(1-Naphthylmethyl)-3-(4-hydroxy-2S-methoxycarbonylpyrrolidinocarbonyl)propionic acid $Rf_1$: 0.52.
Melting point: 79°–85° C.
IR (KBr): $\nu$co 1735, 1620 cm$^{-1}$.

2-(1-Naphthylmethyl)-3-(2R-methoxycarbonylpyrrolidinocarbonyl)propionic acid $Rf_1$: 0.65.
Melting point: 62°–65° C.
IR (KBr): $\nu$co 1735, 1640 cm$^{-1}$.

Reference Example 3

2-(1-Naphthylmethyl)-3-(2S-hydroxymethylpyrrolidinocarbonyl)propionic acid

To a solution of 80 mg of 2-(1-naphthylmethyl)-3-(2S-methoxycarbonylpyrrolidinocarbonyl)propionic acid and 82 mg of sodium borohydride in 2 ml of tert-butyl alcohol was added 1 ml of absolute methano, and then the mixture was stirred at room temperature for 30 minutes. The reaction mixture was concentrated under reduced pressure, and the residue was adjusted to a pH of 1–2 by the addition of a 1N-hydrochloric acid. The solution was extracted with ethyl acetate, and the ethyl acetate layer was washed with water, dried over magnesium sulfate, and concentrated under reduced pressure to obtain 72 mg of 2-(1-naphthylmethyl)-3-(2S-hydroxymethylpyrrolidinocarbonyl)propionic acid.

$Rf_1$: 0.62.
Melting point: 63°–67° C.
IR (KBr): $\nu$co 1710, 1600 cm$^{-1}$.

Reference Example 4

(2RS,3S)-3-Amino-2-hydroxy-5-methylhexanoic acid

A solution of 3.43 g of sodium bisulfite in 20 ml of water was added to 2.81 g of N-carbobenzoxy-L-leucinal, and the mixture was stirred under ice-cooling for 14 hours. To the reaction mixture were added a solution of 1.41 g of potassium cyanide in 50 ml of water and 200 ml of ethyl acetate, and the mixture was stirred at room temperature for 4 hours. The ethyl acetate layer was washed with a saturated sodium chloride aqueous solution, dried over magnesium sulfate, and concentrated under reduced pressure to obtain 2.54 g of 3-carbobenzoxyamino-2-hydroxy-5-methylhexanenitrile as a colorless oil.

A mixture of 500 mg of the nitrile compound obtained, 20 ml of dioxane and 20 ml of concentrated hydrochloric acid was heated under reflux for 12 hours. The reaction mixture was concentrated under reduced pressure and the residue was purified with cation exchange resin colum chromatography (eluent: a 2N-aqueous ammonium hydroxide solution) to obtain 254 mg of (2RS,3S)-3-amino-2-hydroxy-5-methylhexanoic acid (a mixture of 2R and 2S being in a ratio of about 7:3).

Melting point: 137°–140° C.
IR (KBr): $\nu$co 1570 cm$^{-1}$.
NMR (D$_2$O) δ: 0.8–1.0(m, 6H), 1.2–1.4(m, 2H), 1.55–1.8(m, 1H), 3.0–3.4(m, 1H), 3.89(d, 0.7H, J=3.3 Hz), 4.00(d, 0.3H, J=3.3 Hz).
MS: MH+, 162.

Reference Example 5

Isopropyl (2RS,3S)-3-amino-2-hydroxy-5-methylhexanoate hydrochloride

Hydrogen chloride was passed into a solution of 4 g of (2RS,3S)-3-amino-2-hydroxy-5-methylhexanoic acid in 50 ml of isopropyl alcohol with stirring under ice-cooling, and 100 ml of dry benzene was added to the mixture. The mixture was heated under reflux for 10 minutes while removing water formed during the reaction using a molecular sieve. The reaction mixture was concentrated under reduced pressure obtain 5.7 g of isopropyl (2RS,3S)-3-amino-2-hydroxy-5-methylhexanoate hydrochloride as a white powder.

IR (KBr): $\nu$co 1725 cm$^{-1}$.
NMR (D$_2$O) δ: 0.8–1.1(m, 6H), 1.29(d, 6H, J=6.6 Hz), 1.5–2.0(m, 3H), 3.6–3.75(m, 1H), 4.3–4.7(m, 1H), 5.0–5.2(m, 1H).

Reference Example 6

The following ester compound was prepared in an analogous manner to that described in Reference Example 5.

Methyl (2RS,3S)-3-amino-2-hydroxy-5-methylhexanoate hydrochloride

White powder.
IR (KBr): $\nu$co 1740 cm$^{-1}$.
NMR (D$_2$O) δ: 0.85–1.0(m, 6H), 1.4–1.9(m, 3H), 3.65–3.8(m, 1H), 3.83(s, 3H), 4.45–4.7(m, 1H).

Reference Example 7

(2RS,3S)-3-tert-Butyloxycarbonylamino-2-hydroxy-5-methylhexanoic acid

To a solution of 3.22 g of (2RS,3S)-3-amino-2-hydroxy-5-methylhexanoic acid and 3.08 ml of triethylamine in 30 ml of water was added a solution of 5.41 g of 2-(tert-butyloxycarbonyloxyimino)-2-phenylacetonitrile in 30 ml of dioxane, and the mixture was stirred at room temperature for 16 hours. To the reaction mixture was added 100 ml of water, and the mixture was extracted with ethyl acetate to remove neutral materials. The aqueous layer was acidified by the addition of an aqueous succinic acid solution, and the acid solution was extracted with ethyl acetate. The ethyl acetate layer was washed with a saturated sodium chloride aqueous solution, dried over magnesium sulfate and concentrated under reduced pressure to obtain 5.10 g of (2RS,3S)-3-tert-butyloxycarbonylamino-2-hydroxy-5-methylhexanoic acid.

IR (KBr): $\nu$co 1710, 1675 cm$^{-1}$.

NMR (CDCl$_3$) $\delta$: 0.8–1.0(m, 6H), 1.2–1.85(m, 12H), 3.95–4.4(m, 2H), 4.8–5.0(br, 1H), 9.4–10.4(br, 1H).

Reference Example 8

(2RS,3S)-3-Amino-2-hydroxy-5-methylhexanoylisoamylamide hydrochloride

To a solution of 261 mg of (2RS,3S)-3-tert-butyloxycarbonylamino-2-hydroxy-5-methylhexanoic acid, 0.12 ml of isoamylamine and 176 mg of 1-hydroxybenzotriazol in 2 ml of N,N-dimethylformamide and 2 ml of tetrahydrofuran was added 206 mg of dicyclohexylcarbodiimide with stirring under ice-cooling, the mixture was stirred for 16 hours. The reaction mixture was filtered to remove insoluble materials under ice-cooling, and the filtrate was concentrated under reduced pressure. The residue was dissolved in ethyl acetate, and the solution was washed successively with an aqueous citric acid solution, a 5% aqueous sodium bicarbonate solution and a saturated sodium chloride aqueous solution, dried over magnesium sulfate, and concentrated under reduced pressure. The residue was purified with silica gel flash column chromatography (eluent: chloroform) to obtain 185 mg of (2RS,3S)-3-tert-butyloxycarbonylamino-2-hydroxy-5-methylhexanoylisoamylamide as a white powder.

IR (KBr): $\nu$co 1700, 1635 cm$^{-1}$.

To a solution of 180 mg of the amide compound in 20 ml of mthanol was added 8 ml of a 2N-hydrochloric acid, and the mixture was heated at 60° C. for 1 hour. The reaction mixture was concentrated under reduced pressure to obtain 138 mg of (2RS,3S)-3-amino-2-hydroxy-5-methylhexanoylisoamylamide hydrochloride as a white powder.

IR (KBr): $\nu$co 1640 cm$^{-1}$.

Reference Example 9

The following amino compound was prepared in an analogous manner to that described in Reference Example 8.

Statylisoamylamide hydrochloride
IR (neat): $\nu$co 1640 cm$^{-1}$.

Reference Example 10

Isopropyl (2RS,3S)-3-(L-histidyl)amino-2-hydroxy-5-methylhexanoate.2p-toluenesulfonic acid salt To a suspension of 10.0 g of L-histidine methyl ester dihydrochloride in 200 ml of dry chloroform were added 18.4 ml of triethylamine and 10.2 g of 4-methoxybenzyloxycarbonylazide under ice-cooling, and the mixture was stirred for 16 hours at 0° C. The reaction mixture was concentrated under reduced pressure, and to the residue was added a 5% aqueous sodium bicarbonate solution. The mixture was extracted with ethyl acetate, and the ethyl acetate layer was washed with water, dried over anhydrous magnesium sulfate, and concentrated under reduced pressure. The residue was purified with silica gel flash column chromatography (eluent: chloroform/methanol=10/1 by volume) to obtain 11.0 g of N-(4-methoxybenzyloxycarbonyl)-L-histidine methyl ester as a yellow oil. To a solution of 10.9 g of the ester compound in 112 ml of methyl alcohol was added 9.9 ml of hydrazine monohydrate, and the mixture was stirred for 4 hours at room temperature. The reaction mixture was concentrated under reduced pressure, and the residue was washed with ethyl alcohol and dried under reduced pressure at below 40° C. to obtain 4.9 g of N-(4-methoxybenzyloxycarbonyl)-L-histidine hydrazide as a white powder.

To a suspension of the hydrazide compound in 5 ml of N,N-dimethylformamide were added successively 0.90 ml of a dry 5.1N-hydrogen chloride in N,N-dimethylformamide solution and 0.23 ml of isoamyl nitrite at $-20°$ C. with stirring. After disappearance of hydrazide compound, the reaction mixture was cooled to $-30°$ C., and then the reaction mixture was neutralized by adding 0.67 ml of triethylamine to prepare a solution of N-(4-methoxybenzyloxycarbonyl)-L-histidine azide. The cold azide solution was added dropwise to a solution of 350 mg of isopropyl (2RS,3S)-3-amino-2-hydroxy-5-methylhexanoate hydrochloride and 0.46 ml of triethylamine in 8 ml of dry N,N-dimethylformamide under ice-cooling, and the mixture was stirred for 16 hours. The reaction mixture was concentrated under reduced pressure, and to the residue was added a 5% aqueous sodium bicarbonate solution. The mixture was extracted with ethyl acetate, and the ethyl acetate layer was washed with a saturated sodium chloride aqueous solution, dried over anhydrous magnesium sulfate, and concentrated under reduced pressure. The residue was purified with silica gel flash column chromatography (eluent: chloroform/methanol=20:1 by volume) to obtain 325 mg of isopropyl (2RS,3S)-3-[N-(4-methoxybenzyloxycarbonyl)-L-histidyl]amino-2-hydroxy-5-methylhexanoate as a white powder. To a solution of 320 mg of the isopropyl ester compound in 46 ml of isopropyl alcohol were added 300 mg of p-toluenesulfonic acid (anhydride) and 48 mg of a 10% palladium charcoal. The mixture was hydrogenated under a hydrogen atmosphere at room temperature. After filtration of the reaction mixture, the filtrate was concentrated under reduced pressure to obtain 513 mg of isopropyl (2RS,3S)-3-(L-histidyl)amino-2-hydroxy-5-methylhexanoate.2p-toluene sulfonic acid salt as a white powder.

Rf$_1$: 0.09.

IR (KBr): $\nu$co 1720, 1680 cm$^{-1}$.

Reference Example 11

Isopropyl (2RS,3S)-3-(L-histidyl)amino-2-hydroxy-5-methylhexanoate dihydrochloride To a solution of 320 mg of isopropyl (2RS,3S)-3-[N-(4-methoxybenzyloxycarbonyl)-L-histidyl]amino-2-hydroxy-5-methylhexanoate obtained in Reference Example 10 in 20 ml of methyl alcohol were added 2.6 ml of a 2N-hydrochloric acid and 48 mg of a 10% palladium charcoal, and the mixture was hydrogenated under a hydrogen atmosphere at room temperature. After filtration of the catalyst, the filtrate was concentrated under reduced pressure to obtain 275 mg of isopropyl (2RS,3S)-3-(L-histidyl)amino-2-hydroxy-5-methylhexanoate dihydrochloride as a white powder.

$Rf_1$: 0.09.
IR (KBr): $\nu$co 1720, 1680 cm$^{-1}$.

Reference Example 12

The following amino acid compounds were prepared in an analogous manner to that described in Reference Examples 10 and 11.

Methyl (2RS,3S)-3-(L-histidyl)amino-2-hydroxy-5-methylhexanoate dihydrochloride

White powder
$Rf_1$: 0.15.
IR (KBr): $\nu$co 1680 cm$^{-1}$.

(2RS,3S)-3-(L-Histidyl)amino-2-hydroxy-5-methylhexanoylisoamylamide dihydrochloride White powder
$Rf_1$: 0.16.
IR (KBr): $\nu$co 1660 cm$^{-1}$.

L-Histidyl-statylisoamylamide.2p-toluenesulfonic acid salt

White powder
$Rf_1$: 0.29.
IR (KBr): $\nu$co 1680 cm$^{-1}$.

Reference Example 13

To a solution of 3.0 g of β-alanine in 37 ml of a 2N-aqueous sodium hydroxide solution was added 5.8 ml of benzyloxycarbonyl chloride under ice-cooling, and then the mixture was stirred for 30 minutes. The reaction mixture was washed with diethyl ether, adjusted to a pH of 2-3 by adding a 1N-hydrochloric acid, and extracted with ethyl acetate. The ethyl acetate layer was washed with water, dried over anhydrous magnesium sulfate, and concentrated under reduced pressure to obtain 6.53 g of N-benzyloxycarbonyl-β-alanine as a white powder.

To a solution of 2.23 g of the alanine compound in 30 ml of dry N,N-dimethylformamide were added 4.34 ml of methyl iodide and 6.95 g of siliver oxide, and then the mixture was stirred for 16 hours. The insoluble materials was filtered off and the filtrate was dissolved in ethyl acetate. The ethyl acetate layer was washed successively with a 1N-hydrochloric acid, a 5% aqueous sodium bicarbonate solution, and a saturated sodium chloride aqueous solution, dried over anhydrous magnesium sulfate, and concentrated under reduced pressure to obtain 2.08 g of N-benzyloxycarbonyl-N-methyl-β-alanine methyl ester as a colorless oil.

A mixture of 1.0 g of the β-alanine compound, 0.1 g of palladium charcoal and 4 ml of a 2N-hydrochloric acid in 30 ml of methanol was hydrogenated under a hydrogen atmosphere at room temperature. After filtration of the catalyst, the filtrate was concentrated under reduced pressure to obtain 0.62 g of N-methyl-β-alanine methyl ester hydrochloride as a colorless oil.

NMR (D$_2$O) δ: 2.74(s, 3H), 2.85(t, 2H, J=6.6 Hz), 3.33(t, 2H, J=6.6 Hz), 3.74(s, 3H).

Reference Example 14

The following amino compounds were prepared in an analogous manner to that described in Reference Example 13.

Sarcosine methyl ester hydrochloride
White powder
NMR (D$_2$O) δ: 2.80(s, 3H), 3.84(s, 3H), 4.01(s, 2H).

N-Methylalanine methyl ester.p-toluenesulfonic acid salt

White powder
NMR (D$_2$O) δ: 1.56(d, 3H, J=7.2 Hz), 2.38(s, 3H), 2.75(s, 3H), 3.85(s, 3H), 4.10(q, 1H, J=7.2 Hz), 7.69(d, 2H, J=8.2 Hz), 7.35(d, 2H, J=8.2 Hz).

N-Methylaspartic acid α,β-dimethyl ester hydrochloride

Viscous colorless oil
NMR (D$_2$O) δ: 2.83(s, 3H), 3.1-3.4(m, 2H), 3.75(s, 3H), 3.86(s, 3H), 4.3-4.5(m, 1H).

REFERENCE EXAMPLE 15

2-(1-Naphthylmethyl)-3-(N-methyl-N-methoxycarbonylmethylcarbamoyl)propionic acid To a solution of 32.3 g of ethyl succinate and 29.0 g of 1-naphthaldehyde in 320 ml of absolute ethyl alcohol was added 10.7 g of a 50% sodium hydride (dispersion in mineral oil), and the mixture was heated under reflux for 0.5 hours. To the reaction mixture was added 230 ml of a 1N-aqueous sodium hydroxide solution, and the mixture was heated under reflux for 1 hour. The reaction mixture was concentrated under reduced pressure, and the residue was extracted with diethyl ether to remove neutral materials. The aqueous layer was acidified by the addition of concentrated hydrochloric acid, and the acid solution was extracted with diethyl ether. The ethereal layer was washed with a saturated sodium chloride aqueous solution, dried over anhydrous magnesium sulfate and concentrated under reduced pressure. To the residue was added benzene, and precipitated crystals were collected by filtration to obtain 26.5 g of 2-(1-naphthylmethylene)succinic acid.

A mixture of 24.5 g of 2-(1-naphthylmethylene)succinic acid in 260 ml of acetic anhydride was heated at 60° C. for 1 hour. The reaction mixture was concentrated under reduced pressure, and to the residue was added a mixture of benzene and hexane (1:1 by volume), and precipitated crystals were collected by filtration to obtain 16.0 g of 2-(1-naphthylmethylene)succinic anhydride as orange yellow crystals.

To a solution of 1.40 g of sarcosine methyl ester hydrochloride in 50 ml of dichloromethane were added 1.54 ml of triethylamine and 1.70 g of the 2-(1-naphthylmethylene)succinic anhydride obtained, and the mixture was stirred for 30 minutes at room temperature. The reaction mixture was washed successively, with diluted hydrochloric acid, and a saturated sodium chloride aqueous solution, dried over anhydrous magnesium, and concentrated under reduced pressure. The residue was purified by silica gel flash column chromatography (eluent: chloroform) to obtain 2.37 g of 2-(1-naphthylmethylene)-3-(N-methyl-N-methoxycarbonylmethylcarbamoyl)propionic acid as a white powder.

A solution of 1.21 g of the propionic acid compound in 50 ml of methanol was hydrogenated over a 180 mg of 10% palladium charcoal under a hydrogen atmosphere at room temperature. After filtration of the catalyst, the reaction mixture was concentrated under reduced pressure to obtain 1.14 g of 2-(1-naphthylmethyl)-3-(N-methyl-N-methoxycarbonylmethylcarbamoyl)propionic acid as a white powder.

Rf$_1$: 0.63.

IR (KBr): $\nu$co 1730, 1630 cm$^{-1}$.

Reference Example 16

The following acid compounds were prepared in an analogous manner to that described in Reference Example 15.

2-(1-Naphthylmethyl)-3-[N-methyl-N-(2-hydroxyethyl)carbamoyl]propionic acid

Viscous colorless oil

Rf$_1$: 0.60.

IR (neat): $\nu$co 1710, 1620 cm$^{-1}$.

N-Methyl-N-[4-(1-naphthyl)-3-carboxy]butyryl-L-alanine methyl ester

White powder

Rf$_1$: 0.61.

IR (KBr): $\nu$co 1730, 1630 cm$^{-1}$.

2-(1-Naphthylmethyl)-3-(N-methyl-N-(2-methoxycarbonylethyl)carbamoyl]propionic acid Viscous colorless oil Rf$_1$: 0.51.

IR (neat): $\nu$co 1710, 1620 cm$^{-1}$.

N-Methyl-N-[4-(1-naphthyl)-3-carboxy]butyryl-L-aspartic acid dimethyl ester

Viscous colorless oil

Rf$_1$: 0.53.

IR (neat): $\nu$co 1730, 1640 cm$^{-1}$.

2-(1-Naphthylmethyl)-3-[bis(2-hydroxyethyl)carbamoyl]propionic acid

White powder

Rf$_1$: 0.44.

IR (KBr): $\nu$co 1720, 1640 cm$^{-1}$.

N-[4-(1-Naphthyl)-3-carboxy]butyrylglycine methyl ester

White powder

Rf$_1$: 0.68.

IR (KBr): $\nu$co 1740, 1640 cm$^{-1}$.

N-[4-(1-Naphthyl)-3-carboxy]butyryl-L-alanine methyl ester

White powder

Rf$_1$: 0.52.

IR (KBr): $\nu$co 1720, 1640 cm$^{-1}$.

N-[4-(1-Naphthyl)-3-carboxy]butyrylglycine methylamide

White powder

Rf$_1$: 0.57.

IR (KBr): $\nu$co 1720, 1640 cm$^{-1}$.

N-[4-(1-Naphthyl)-3-carboxy]butyryl-L-alanineamide

White powder

Rf$_1$: 0.25.

IR (KBr): $\nu$co 1700, 1640 cm$^{-1}$.

Reference Example 17

Isopropyl (2RS,3S)-3-amino-2-hydroxy-5-methylhexanoate hydrochloride

Hydrogen chloride was passed into a solution of 4.0 g of (2RS,3S)-3-amino-2-hydroxy-5-methylhexanoic acid in 50 ml of isopropanol was stirring under ice-cooling, and to the reaction mixture was 100 ml of dry benzene. The mixture was heated under reflux for 10 minutes while removing water formed during the reaction. The reaction mixture was concentrated under reduced pressure to obtain 5.7 g of isopropyl (2RS,3S)-3-amino-2-hydroxy-5-methylhexanoate hydrochloride as a white powder.

IR (KBr): $\nu$co 1725 cm$^{-1}$.

NMR (D$_2$O) $\delta$: 0.8–1.1(m, 6H), 1.29(d, 6H, J=6.6 Hz), 1.5–2.0(m, 3H), 3.6–3.75(m, 1H), 4.3–4.7(m, 1H), 5.0–5.2(m, 1H).

Reference Example 18

The following ester compound was prepared in an analogous manner to that described in Reference Example 17.

Methyl (2RS,3S)-3-amino-2-hydroxy-5-methylhexanoate hydrochloride

White powder

IR (KBr): $\nu$co 1740 cm$^{-1}$.

NMR (D$_2$O) $\delta$: 0.85–1.0(m, 6H), 1.4–1.9(m, 3H), 3.65–3.8(m, 1H), 3.83(s,3H), 4.45–4.7(m, 1H).

Reference Example 19

(2RS,3S)-3-tert-Butyloxycarbonylamino-2-hydroxy-5-methylhexanoylisoamylamide hydrochloride To a solution of 3.22 g of (2RS,3S)-3-amino-2-hydroxy-5-methylhexanoic acid and 3.08 ml of triethylamine in 30 ml of water was added a solution of 5.41 g of 2-(tert-butyloxycarbonyloxyimino)-2-phenylacetonitrile in 30 ml of dioxane, and the mixture was stirred for 16 hours at room temperature. To the reaction mixture was added 100 ml of water, and the mixture was extracted with ethyl acetate to remove neutral materials. The aqueous layer was acidified by the addition of an aqueous citric acid solution, and the acid solution was extracted with ethyl acetate. The ethyl acetate layer was washed with a saturated sodium chloride aqueous solution, dried over anhydrous magnesium sulfate, and concentrated under reduced pressure to obtain 5.10 g of (2RS,3S)-3-tert-butyloxycarbonylamino-2-hydroxy-5-methylhexanoic acid as a pale yellow oil.

IR (neat): $\nu$co 1710, 1675 cm$^{-1}$.

NMR (CDCl$_3$) $\delta$: 0.8–1.0(m, 6H), 1.2–1.85(m, 12H), 3.95–4.4(m, 2H), 4.8–5.0(br, 1H), 9.4–10.4(br, 1H).

To a solution of 261 mg of the (2RS,3S)-3-tert-butyloxycarbonylamino-2-hydroxy-5-methylhexanoic acid and 0.12 ml of isoamylamine and 176 mg of 1-hydroxybenzotriazole in a mixture of 2 ml of N,N-dimethylformamide and 2 ml of tetrahydrofuran was 206 mg of dicyclohexylcarbodiimide with stirring and under ice-cooling. The mixture was stirred for 16 hours. The reaction mixture was cooled and filtered to remove insoluble materials. The filtrate was concentrated under reduced pressure, and the residue was dissolved in ethyl acetate. The ethyl acetate layer was washed successively with an aqueous citric acid solution, a 5% aqueous sodium bicarbonate solution and a saturated sodium chloride aqueous solution, dried over anhydrous magnesium sulfate and concentrated under reduced pressure. The residue was purified by silica gel flash column chromatography (eluent: chloroform) to obtain 185 mg of (2RS,3S)-3-tert-butyloxycarbonylamino-2-hydroxy-5-methylhexanoylisoamylamide as a white powder [IR (KBr): $\nu$co 1700, 1635 cm$^{-1}$].

To a solution of 180 mg of the amide compound in 20 ml of methyl alcohol was added 8 ml of a 2N-hydrochloric acid, and the mixture was heated at 60° C. for 1 hour. The reaction mixture was concentrated under reduced pressure to obtain 138 mg of (2RS,3S)-3-amino-2-hydroxy-5-methylhexanoylisoamylamide hydrochloride as a white powder [IR (KBr): $\nu$co 1640 cm$^{-1}$].

Reference Example 20

2-(Methoxycarbonyl)-2-(1-naphthylmethyl)propionic acid

A solution of 300 mg of 2-(1-naphthylmethylene)succinic anhydride and 18 ml of methyl alcohol in 30 ml of dry dichloromethane was heated under reflux for 5 hours. The reaction mixture was washed successively with a diluted hydrochloric acid and water, dried over anhydrous magnesium sulfate, and concentrated under reduced pressure to obtain 336 mg of 3-methoxycarbonyl-2-(1-naphthylmethylene)propionic acid as a white powder.

To a solution of 251 mg of the propionic acid compound in 10 ml of methyl alcohol was added 30 mg of a 10% palladium charcoal, and the mixture was hydrogenated under a hydrogen atmosphere at room temperature. After filtration of the catalyst, the reaction mixture was concentrated under reduced pressure to obtain 250 mg of 3-methoxycarbonyl-2-(1-naphthylmethyl)propionic acid as a white powder.

Rf$_1$: 0.68
Melting point: 111°–112° C.
IR (KRr): $\nu$co 1730, 1690 cm$^{-1}$.

Reference Example 21

The following carboxylic acid compounds were prepared in an analogous manner to that described in Reference Example 20

3-(Isopropoxycarbonyl)-2-(1-naphthylmethyl)propionic acid

White powder
Rf$_1$: 0.63.
Melting point: 39°–43° C.
IR (KBr): $\nu$co 1710 cm$^{-1}$.

3-(Carbamoyl)-2-(1-naphthylmethyl)propionic acid

White powder
Rf$_1$: 0.42
Melting point: 179°–181° C.
IR (KBr): $\nu$co 1700, 1640 cm$^{-1}$.

EXAMPLE 1

Isopropyl(2RS,3S)-3-{N-[2-(1-naphthylmethyl)-3-(2S-methoxycarbonylpyrrolidinocarbonyl)propionyl]-L-histidyl}-amino-2-hydroxy-5-methylhexanoate To a solution of 346 mg of 2-(1-naphthylmethyl)-3-(2S-methoxycarbonylpyrrolidinocarbonyl)propionic acid and 670 mg of isopropyl 3-L-histidylamino-2-hydroxy-5-methylhexanoate.2p-toluenesulfonic acid salt in 17 ml of N,N-dimethylformamide were added successively 0.24 ml of diphenylphosphoryl azide and 0.43 ml of triethylamine with stirring under ice-cooling, and the mixture was stirred overnight under ice-cooling. The reaction mixture was concentrated under reduced pressure, and the residue was added a 5% aqueous sodium bicarbonate solution. The mixture was extracted with ethyl acetate. The ethyl acetate layer was washed with water, dried over anhydrous magnesium sulfate, and concentrated under reduced pressure. The residue was purified by silica gel column chromatography (eluent: chloroform/methanol=30/1) to obtain 117 mg of isopropyl (2RS,3S)-3-{N-[2-(1-naphthylmethyl)-3-(2S-methoxycarbonylpyrrolidinocarbonyl)propionyl]-L-histidyl}amino-2-hydroxy-5-methylhexanoate as a white powder.

Melting point: 90°–94° C.
Rf$_1$: 0.68.
Rf$_2$: 0.65.
MS: MH+, 692.

EXAMPLE 2

Isopropyl(2RS,3S)-3-{N-[2-(1-naphthylmethyl)-3-(4-hydroxy-2S-methoxycarbonylpyrrolidinocarbonyl)propionyl]-L-histidyl}amino-2-hydroxy-5-methylhexanoate To a solution of 17 mg of 2-(1-naphthylmethyl)-3-(4-hydroxy-2S-methoxycarbonylpyrrolidinocarbonyl)propionic acid and 28 mg of 3-L-histidylamino-2-hydroxy-5-methylhexanoate.2p-toluenesulfonic acid salt in 2 ml of N,N-dimethylformamide were added successively 0.012 ml of diphenylphosphoryl azide and 0.021 ml of triethylamine, and the mixture was stirred overnight. The reaction mixture was concentrated under reduced pressure, and to the residue was added a 5% aqueous sodium bicarbonate solution. The mixture was extracted with ethyl acetate, and the ethyl acetate layer was washed with water, dried over anhydrous magnesium sulfate, and concentrated under reduced pressure. The residue was purified by preparative silica gel thin layer chromatography (developing solvent: chloroform/methanol=5/1 by volume, Rf$_2$=0.63) to obtain 28 mg of isopropyl (2RS,3S)-3-{N-[2-(1-naphthylmethyl)-3-(4-hydroxy-2S-methoxycarbonylpyrrolidinocarbonyl)propionyl]-L-histidyl}amino-2-hydroxy-5-methylhexanoate as a white powder.

Melting point: 105°–108° C.
Rf$_1$: 0.65.
Rf$_2$: 0.63.
MS: MH+, 708.

EXAMPLE 3

Methyl(2RS,3S)-3-{N-[2-(1-naphthylmethyl)-3-(2S-methoxycarbonylpyrrolidinocarbonyl)propionyl]-L-histidyl}amino-2-hydroxy-5-methylhexanoate To a suspension of 31 mg of 2-(1-naphthylmethyl)-3-(2-methoxycarbonylpyrrolidinocarbonyl)propionic acid and 40 mg of methyl 3-(L-histidyl)amino-2-hydroxy-5-methylhexanoate dihydrochloride in 3 ml of N,N-dimethylformamide were added successively 0.022 ml of diphenylphosphoryl azide and 0.038 ml of triethylamine with stirring under ice-cooling, and the mixture was stirred for 16 hours. The reaction mixture was concentrated under reduced pressure, and to the residue was added a 5% aqueous sodium bicarbonate solution. The mixture was extracted with ethyl acetate, and the ethyl acetate layer was washed with a saturated sodium chloride solution, dried over anhydrous magnesium sulfate, and concentrated under reduced pressure. The residue was purified by preparative silica gel thin layer chromatography (developing solvent: chloroform/methanol=5/1 by volume; $Rf_2=0.48$) to obtain 13 mg of methyl(2RS,3S)-3-{N-[2-(1-naphthylmethyl)-3-(2S-methoxycarbonylpyrrolidinocarbonyl)propionyl]-L-histidyl}amino-2-hydroxy-5-methylhexanoate as a white powder.

Melting point: 102°–107° C.
$Rf_1$: 0.60.
$Rf_2$: 0.48.
MS: MH+, 664.

EXAMPLE 4

(2RS,3S)-3-{N-[2-(1-Naphthylmethyl)-3-(2S-methoxycarbonylpyrrolidinocarbonyl)propionyl]-L-histidyl-}amino-2-hydroxy-5-methylhexanoylisoamylamide To a suspension of 37 mg of 2-(1-naphthylmethyl)-3-(2-methoxycarbonylpyrrolidinocarbonyl)propionic acid and 44 mg of 3-(L-histidyl)amino-2-hydroxy-5-methylhexanoylisoamylamide dihydrochloride in 3 ml of N,N-dimethylformamide were added successively 0.03 ml of diphenylphosphoryl azide and 0.05 ml of triethylamine, and the mixture was stirred for 16 hours. The reaction mixture was concentrated under reduced pressure, and a 5% aqueous sodium bicarbonate solution was added to the residue. The mixture was extracted with ethyl acetate, and the ethyl acetate layer was washed with water, dried over anhydrous magnesium sulfate, and concentrated under reduced pressure. The residue was purified by preparative silica gel chromatography (developing solvent: chloroform/methanol=5/1 by volume; $Rf_2=0.51$) to obtain 13 mg of (2RS,3S)-3-{N-[2-(1-naphthylmethyl)-3-(2S-methoxycarbonylpyrrolidinocarbonyl)propionyl]-L-histidyl-}amino-2-hydroxy-5-methylhexanoylisoamylamide as a white powder.

Melting point: 103°–108° C.
$Rf_1$: 0.65.
$Rf_2$: 0.51.
MS: MH+, 719.

EXAMPLE 5

N-[2-(1-Naphthylmethyl)-3-(2S-methoxycarbonylpyrrolidinocarbonyl)propionyl]-L-histidyl-statylisoamylamide To a solution of 20 mg of 2-(1-naphthylmethyl)-3-(2S-methoxycarbonylpyrrolidinocarbonyl)propionic acid and 40 mg of L-histidyl-statylisoamylamide.2p-toluenesulfonic acid salt in 2 ml of N,N-dimethylformamide were added successively 0.014 ml of diphenylphosphoryl azide and 0.025 ml of triethylamine with stirring under ice-cooling. The mixture was stirred overnight. The reaction mixture was concentrated under reduced pressure, and to the residue was added a 5% aqueous sodium bicarbonate solution. The mixture was extracted with ethyl acetate, and the ethyl acetate layer was washed with water, dried over anhydrous magnesium sulfate, and concentrated under reduced pressure. The residue was purified by preparative silica gel thin layer chromatography (developing solvent: chloroform/methanol=5/1 by volume; $Rf_2=0.66$) to obtain 15 mg of N-[2-(1-naphthylmethyl)-3-(2S-methoxycarbonylpyrrolidino)carbonyl]-L-histidyl-statylisoamylamide as a white powder.

Melting point: 80°–85° C.
$Rf_1$: 0.68.
$Rf_2$: 0.66.
MS: MH+, 733.

EXAMPLE 6

Isopropyl(2RS,3S)-3-{N-[2-(1-naphthylmethyl)-3-(2S-hydroxymethylpyrrolidinocarbonyl)propionyl]-L-histidyl}amino-2-hydroxy-5-methylhexanoate To a solution of 21 mg of 2-(1-naphthylmethyl)-3-(2S-hydroxymethylpyrrolidinocarbonyl)propionic acid and 40 mg of isopropyl 3-(L-histidyl)amino-2-hydroxy-5-methylhexanoate.2p-toluenesulfonic acid salt in 2 ml of N,N-dimethylformamide were added 0.016 ml of diphenylphosphoryl azide and 0.028 ml of triethylamine with stirring under ice-cooling. The mixture was stirred overnight. The reaction mixture was concentrated under reduced pressure, and to the residue was added a 5% aqueous sodium bicarbonate solution. The mixture was extracted with ethyl acetate, and the ethyl acetate layer was washed with water, dried over anhydrous magnesium sulfate, and concentrated under reduced pressure. The residue was purified by preparative silica gel thin layer chromatography (eluent: chloroform/methanol=5/1; $Rf_2=0.59$) to obtain 16 mg of isopropyl(2RS,3S)-3-{N-[2-(1-naphthylmethyl)-3-(2S-hydroxymethylpyrrolidinocarbonyl)propionyl]-L-histidyl}amino-2-hydroxy-5-methylhexanoate as a white powder.

Melting point: 86°–92° C.
$Rf_1$: 0.60.
$Rf_2$: 0.59.
MS: MH+, 664.

EXAMPLE 7

Isopyl(2RS,3S)-3-{N-[2-(1-naphthylmethyl)-3-(2R-methoxycarbonylpyrrolidinocarbonyl)propionyl]-L-histidyl}amino-2-hydroxy-5-methylhexanoate To a solution of 20 mg of 2-(1-naphthylmethyl)-3-(2R-methoxycarbonylpyrrolidinocarbonyl)propionic acid and 39 mg of isopropyl 3-L-histidylamino-2-hydroxy-5-methylhexanoate.2p-toluenesulfonic acid salt in 5 ml of N,N-dimethylformamide were added 0.014 ml of diphenylphosphoryl azide and 0.025 ml of triethylamine with stirring under ice-cooling, and the mixture was stirred overnight. The reaction mixture was concentrated under reduced pressure, and a 5% aqueous sodium bicarbonate solution was added to the residue. The mixture was extracted with ethyl acetate, and the ethyl acetate layer was washed with water, dried over anhydrous magnesium sulfate, and concentrated under reduced pressure. The residue was purified by preparative silica gel thin layer chromatography (developing solvent: chloroform/methanol=5/1 by volume; $Rf_2=0.56$) to obtain 7 mg of isopropyl(2RS,3S)-3-{N-[2-(1-naphthylmethyl)-3-(2R-methoxycarbonylpyrrolidinocarbonyl)propionyl]-L- histidyl}amino-2-hydroxy-5-methylhexanoate as a white powder.
Melting point: 99°–103° C.
Rf$_1$: 0.62.
Rf$_2$: 0.56.
MS: MH+, 692.

EXAMPLE 8

Isopropyl(2RS,3S)-3-{N-[2-(1-naphthylmethyl)-3-(N-methyl-N-methoxycarbonylmethylcarbamoyl)propionyl]-L-histidyl}amino-2-hydroxy-5-methylhexanoate To a solution of 50 mg of 2-(1-naphthylmethyl)-3-(N-methyl-N-methoxycarbonylmethylcarbamoyl)propionic acid and 70 mg of isopropyl(2RS,3S)-3-(L-histidyl)amino-2-hydroxy-5-methylhexanoate dihydrochloride in 4 ml of N,N-dimethylformamide were added 0.036 ml of diphenylphosphoryl azide and 0.064 ml of triethylamine with stirring under ice-cooling, and the mixture was stirred overnight. The reaction mixture was concentrated under reduced pressure, and a 5% aqueous sodium bicarbonate solution was added to the residue. The mixture was extracted with ethyl acetate, and the ethyl acetate layer was washed with water, dried over anhydrous magnesium sulfate, concentrated under reduced pressure. The residue was purified by preparative silica gel thin layer chromatography (developing solvent: chloroform/methanol=5/1 by volume; Rf$_2$=0.36) to obtain 10 mg of isopropyl(2RS,3S)-3-{N-[2-(1-naphthylmethyl)-3-(N-methyl-N-methoxycarbonylmethylcarbamoyl)propionyl]-L-histidyl}amino-2-hydroxy-5-methylhexanoate as a white powder.
Melting point: 76°–80° C.
Rf$_1$: 0.72.
Rf$_2$: 0.36.
MS: MH+, 666.

EXAMPLE 9

The following compounds were prepared in an analogous manner to that described in Example 8

Isopropyl(2RS,3S)-3-{N-{2-(1-naphthylmethyl)-3-[N-methyl-N-{2-methoxycarbonylethyl)carbamoyl]propionyl}-L-histidyl}amino-2-hydroxy-5-methylhexanoate White powder
Melting point: 78°–83° C.
Rf$_1$: 0.51.
Rf$_2$: 0.51.
MS: MH+, 680.

Isopropyl(2RS,3S)-3-{N-{2-(1-naphthylmethyl)-3-[N-methyl-N-(1S-methoxycarbonylethyl)carbamoyl]propionyl}-L-histidyl}amino-2-hydroxy-5-methylhexanoate White powder
Melting point: 86°–88° C.
Rf$_1$: 0.49.
Rf$_2$: 0.46.
MS: MH+, 680.

Isopropyl(2RS,3S)-3-{N-{2-(1-naphthylmethyl)-3-[N-methyl-N-(1S,2-bismethoxycarbonylethyl)carbamoyl]propionyl}-L-histidyl}amino-2-hydroxy-5-methylhexanoate White powder
Melting point: 80°–85° C.
Rf$_1$: 0.51.
Rf$_2$: 0.49.
MS: MH+, 738.

Isopropyl(2RS,3S)-3-{N-{2-(1-naphthylmethyl)-3-[N-methyl-N-(2-hydroxyethyl)carbamoyl]propionyl}-L-histidyl}amino-2-hydroxy-5-methylhexanoate White powder
Melting point: 86°–89° C.
Rf$_1$: 0.49.
Rf$_2$: 0.44.
MS: MH+, 638.

Isopropyl(2RS,3S)-3-{N-{2-(1-naphthylmethyl)-3-[bis(2-hydroxyethyl)carbamoyl]propionyl}-L-histidyl}amino-2-hydroxy-5-methylhexanoate White powder
Melting point: 72°–76° C.
Rf$_1$: 0.49.
Rf$_2$: 0.44.
MS: NH+, 668.

Isopropyl(2RS,3S)-3-{N-[2-(1-naphthylmethyl)-3-(N-methoxycarbonylmethylcarbamoyl)propionyl]-L-histidyl}amino-2-hydroxy-5-methylhexanoate White powder
Melting point: 89°–93° C.
Rf$_1$: 0.68.
Rf$_2$: 0.53.
MS: MH+, 652.

Isopropyl(2RS,3S)-3-{N-[2-(1-naphthylmethyl)-3-(N-methylcarbamoylmethylcarbamoyl)propionyl]-L-histidyl}amino-2-hydroxy-5-methylhexanoate White powder
Melting point: 87°–92° C.
Rf$_1$: 0.68.
Rf$_2$: 0.45.
MS: MH+, 651.

Isopropyl(2RS,3S)-3-{N-{2-(1-naphthylmethyl)-3-[N-(1S-methoxycarbonylethyl)carbamoyl]propionyl}-L-histidyl}amino-2-hydroxy-5-methylhexanoate White powder
Melting point: 89°–94° C.
Rf$_1$: 0.43.
Rf$_2$: 0.42.
MS: MH+, 666.

Isopropyl(2RS,3S)-3-{N-{2-(1-naphthylmethyl)-3-[N-(1S-carbamoylethyl)carbamoyl]propionyl}-L-histidyl}amino-2-hydroxy-5-methylhexanoate White powder
Melting point: 115°–119° C.
Rf$_1$: 0.50.
Rf$_2$: 0.44.
MS: MH+, 651.

EXAMPLE 10

Methyl(2RS,3S)-3-{N-[2-(1-naphthylmethyl)-3-(N-methyl-N-methoxycarbonylmethylcarbamoyl)propionyl]-L-histidyl}amino-2-hydroxy-5-methylhexanoate To a solution of 30 mg of 2-(1-naphthylmethyl)-3-(N-methyl-N-methoxycarbonylmethylcarbamoyl)propionic acid and 42 mg of methyl(2RS,3S)-3-(L-histidyl)amino-2-hydroxy-5-methylhexanoate dihydrochloride in 3 ml of N,N-dimethylformamide were added successively 0.023 ml of diphenylphosphoryl azide and 0.040 ml of triethylamine with stirring under ice-cooling, and the mixture was stirred overnight. The reaction mixture was concentrated under reduced pressure, and a 5% aqueous sodium bicarbonate solution was added to the residue. The mixture was extracted with ethyl acetate, and the ethyl acetate layer was washed with water, dried over anhydrous magnesium sulfate, and concentrated under reduced pressure. The residue was purified by preparative silica gel thin layer chromatography (developing solvent: chloroform/methanol=5/1 by volume; $Rf_2=0.31$) to obtain 14 mg of methyl (2RS,3S)-3-{N-[2-(1-naphthylmethyl)-3-(N-methyl-N-methoxycarbonylmethylcarbamoyl)propionyl]-L-histidyl}amino-2-hydroxy-5-methylhexanoate as a white powder.

Melting point: 75°–79° C.
$Rf_1$: 0.67.
$Rf_2$: 0.31.
MS: $MH^+$, 638.

EXAMPLE 11

(2RS,3S)-3-{N-[2-(1-Naphthylmethyl)-3-(N-methyl-N-methoxycarbonylmethylcarbamoyl)propionyl]-L-histidyl}amino-2-hydroxy-5-methylhexanoylisoamylamide To a solution of 29 mg of 2-(1-naphthylmethyl)-3-(N-methyl-N-methoxycarbonylmethylcarbamoyl)propionic acid and 45 mg of (2RS,3S)-3-(L-histidyl)amino-2-hydroxy-5-methylhexanoylisoamylamide in 4 ml of N,N-dimethylformamide were added successively 0.023 ml of diphenylphosphoryl azide and 0.040 ml of triethylamine with stirring under ice-cooling, and the mixture was stirred overnight. The reaction mixture was concentrated under reduced pressure, and a 5% aqueous sodium bicarbonate solution was added to the residue. The mixture was extracted with ethyl acetate, and the ethyl acetate layer was washed with water, dried over anhydrous magnesium sulfate, and concentrated under reduced pressure. The residue was purified by preparative silica gel thin layer chromatography (developing solvent: chloroform/methanol=5/1 by volume; $Rf_2=0.46$) to obtain 4 mg of (2RS,3S)-3-{N-[2-(1-naphthylmethyl)-3-(N-methyl-N-methoxycarbonylmethylcarbamoyl)propionyl]-L-histidyl}amino-2-hydroxy-5-methylhexanoylisoamylamide as a white powder Melting point: 77°–80° C.
$Rf_1$: 0.69.
$Rf_2$: 0.46.
MS: $MH^+$, 693.

EXAMPLE 12

N-[2-(1-Naphthylmethyl)-3-(N-methyl-N-methoxycarbonylmethylcarbamoyl)propionyl]-L-histidyl-statylisoamylamide To a solution of 23 mg of 2-(1-naphthylmethyl)-3-(N-methyl-N-methoxycarbonylmethylcarbamoyl)propionic acid and 50 mg of L-histidyl-statylisoamylamide.2p-toluenesulfonic acid salt in 5 ml of N,N-dimethylformamide were added successively 0.018 ml of diphenylphosphoryl azide and 0.05 ml of triethylamine with stirring under ice-cooling, and the mixture was stirred overnight. The reaction mixture was concentrated under reduced pressure, and to the residue was added a 5% aqueous sodium bicarbonate solution. The mixture was extracted with ethyl acetate, and the ethyl acetate layer was washed with water, dried over anhydrous magnesium sulfate, concentrated under reduced pressure. The residue was purified by preparative silica gel thin layer chromatography (developing solvent: chloroform/methanol=5/1 by volume; $Rf_2=0.48$) to obtain 10 mg of N-[2-(1-naphthylmethyl)-3-(N-methyl-N-methoxycarbonylmethylcarbamoyl)propionyl]-L-histidyl-statylisoamylamide as a white powder.

Melting point: 84°–88° C.
$Rf_1$: 0.52.
$Rf_2$: 0.48.
MS: $MH^+$, 707.

EXAMPLE 13

Isopropyl (2RS,3S)-3-[3-(methoxycarbonyl)-2-(1-naphthylmethyl)propionyl-L-histidyl]amino-2-hydroxy-5-methylhexanoate To a solution of 28 mg of 3-methoxycarbonyl-2-(1-naphthylmethyl)propionic acid and 50 mg of isopropyl (2RS,3S)-3-(L-histidyl)amino-2-hydroxy-5-methylhexanoate dihydrochloride were added successively 0.026 ml of diphenylphosphoryl azide and 0.046 ml of triethylamine, and the mixture was stirred overnight. The reaction mixture was concentrated under reduced pressure, and a 5% aqueous sodium bicarbonate solution was added to the residue. The mixture was extracted with ethyl acetate, and the ethyl acetate layer was washed with water, dried over anhydrous magnesium sulfate, and concentrated under reduced pressure. The residue was purified by silica gel column chromatography (eluent: chloroform/methanol=20/1 by volume) to obtain 20 mg of isopropyl (2RS,3S)-3-[3-(methoxycarbonyl)-2-(1-naphthylmethyl)propionyl-L-histidyl]amino-2-hydroxy-5-methylhexanoate as a white powder.

Melting point: 75°–78° C.
$Rf_1$: 0.58.
$Rf_2$: 0.52.
MS: $MH^+$, 595.

EXAMPLE 14

The following compounds were prepared in an analogous manner to that described in Example 13.

Isopropyl (2RS,3S)-3-{N-[3-(carbamoyl)-2-(1-naphthylmethyl)-propionyl]-L-histidyl}amino-2-hydroxy-5-methylhexanoate White powder
Melting point: 96°–102° C.
$Rf_1$: 0.59.
$Rf_2$: 0.52.
MS: $MH^+$, 580.

Isopropyl (2RS,3S)-3-{N-[3-(isopropoxycarbonyl)-2-(1-naphthylmethyl)propionyl]-L-histidyl}amino-2-hydroxy-5-methylhexanoate White powder
Melting point: 72°–75° C.
$Rf_1$: 0.69.
$Rf_2$: 0.69.
MS: $MH^+$, 623.

EXAMPLE 15

N-[3-(methoxycarbonyl)-2-(1-naphthylmethyl)propionyl]-L-histidyl-statylisoamylamide To a solution of 16 mg of 3-(methoxycarbonyl)-2-(1-naphthylmethyl)propionic acid and 27 mg of L-histidyl-statylisoamylamide dihydrochloride in 3 ml of N,N-dimethylformamide were added successively 0.015 ml of diphenylphosphoryl azide and 0.027 ml of triethylamine with stirring under ice-cooling, and the mixture was stirred overnight. The reaction mixture was concentrated under reduced pressure, and to the residue was added a 5% aqueous sodium bicarbonate solution. The mixture was extracted with ethyl acetate, and the ethyl acetate layer was washed with water, dried over anhydrous magnesium sulfate, and concentrated under reduced pressure. The residue was purified by preparative silica gel thin layer chromatography (developing solvent: chloroform/methanol=5/1 by volume; $Rf_2=0.65$) to obtain 10 mg of N-[3-methoxycarbonyl-2-(1-naphthylmethylpropionyl]-L-histidyl-statylisoamylamide as a white powder.

Melting point: 70°–74° C.
$Rf_1$: 0.65.
$Rf_2$: 0.65.
MS: $MH^+$, 636.

EXAMPLE 16

The following compound was prepared in an analogous manner to that described in Example 15.

(2RS,3S)-3-[3-Methoxycarbonyl-2-(1-naphthylmethyl)-propionyl-L-histidyl]amino-2-hydroxy-5-methylhexanoylisoamylamide White powder
Melting point: 72°–75° C.
$Rf_1$: 0.61.
$Rf_2$: 0.53.
MS: $MH^+$, 622.

Test Example 1

Human resin-sheep resin substrate reaction system in vitro

To a mixture containing 200 μl of a 125 mM pyrophosphate buffer (pH 7.4), 25 μl of a 20 mM aqueous solution of L-phenylalanyl-L-alanyl-L-prolin as an angiotensin converting enzyme inhibitor, 50 μl of semipurified sheep renin substrate (2000 mg angiotensin I/ml), 50 μl of dimethyl sulfoxide solution of an amino acid derivative of the present invention (or 50 μl of dimethyl sulfoxide as a control) and 150 μl of deionized water was added 25 μl of purified human renin (20–30 ng angiotensin I/ml/hr). The mixture was incubated for 15 minutes on a water bath at 37° C., and the reaction mixture was allowed to stand for 5 minutes on a water bath at 100° C. to stop the reaction. After cooling, 200 μl of the solution were taken up and the amount of angiotensin I produced by the addition of renin was determined by radioimmunoassay. The inhibitory effect was calculated by the following equation.

Inhibition (%) =

$$\frac{\text{Amount of angiotensin I in control} - \text{Amount of angiotensin I in a mixture containing a compound of this invention}}{\text{Amount of angiotensin I in control}} \times 100$$

The molar concentration which produced 50% inhibition ($IC_{50}$) was calculated from the inhibition value obtained, and the results are shown below.

| Compound | $IC_{50}$ (molar concentration) |
| --- | --- |
| Isopropyl (2RS, 3S)-3-{N—[2-(1-naphthylmethyl-3-(2S—methoxycarbonylpyrrolidinocarbonyl)-propionyl[-L—histidyl}amino-2-hydroxy-5-methylhexanoate | $5.2 \times 10^{-8}$ M |
| Isopropyl (2RS, 3S)-3-{N—[2-(1-naphthylmethyl)-3-(4-hydroxy-2S—methoxycarbonylpyrrolidinocarbonyl)propionyl]-L—histidyl}amino-2-hydroxy-5-methylhexanoate | $4.1 \times 10^{-8}$ M |
| Methyl (2RS, 3S)-3-{N—[2-(1-naphthylmethyl)-3-(2S—methoxycarbonylpyrrolidinocarbonyl)-propionyl]-L—histidyl}amino-2-hydroxy-5-methylhexanoate | $4.0 \times 10^{-8}$ M |
| (2RS, 3s)-3-{N—[2-(1-naphthylmethyl)-3-(2S—methoxycarbonylpyrrolidinocarbonyl)propionyl]-L—histidyl}amino-2-hydroxy-5-methylhexanoylisoamylamide | $8.4 \times 10^{-8}$ M |
| N—[2-(1-naphthylmethyl)-3-(2S—methoxycarbonylpyrrolidinocarbonyl)propionyl]-L—histidyl-statyleisoamylamide | $1.2 \times 10^{-7}$ M |
| Isopropyl (2RS, 3S)-3-{N—[2-(1-naphthylmethyl)-3-(2S—hydroxymethylpyrrolidinocarbonyl)-propionyl]-L—histidyl}amino-2-hydroxy-5-methylhexanoate | $2.3 \times 10^{-8}$ M |
| Isopropyl (2RS, 3S)-3-{N—[2-(1-naphthylmethyl)-3-(2R—methoxycarbonylpyrrolidinocarbonyl)-propionyl]-L—histidyl}amino-2-hydroxy-5-methylhexanoate | $2.8 \times 10^{-8}$ M |
| Isopropyl-3-{N—[2-(1-naphthylmethyl)-3-(N—methyl-N—methoxycarbonylmethylcarbamoyl)-propionyl]-L—histidyl}amino-2-hydroxy-5-methylhexanoate | $1.7 \times 10^{-8}$ M |
| Isopropyl (2RS, 3S)-3-{N—{2-(1-naphthylmethyl)-3-[N—methyl-N—(2-methoxycarbonylethyl)-carbamoyl]propionyl}-L—histidyl}-amino-2-hydroxy-5-methylhexanoate | $1.7 \times 10^{-8}$ M |
| Isopropyl (2RS, 3S)-3-{N—{2-(1-naphthylmethyl)-3-[N—methyl-N—(1S—methoxycarbonylethyl)-carbamoyl]propionyl}-L—histidyl}amino-2-hydroxy-5-methylhexanoate | $3.3 \times 10^{-8}$ M |
| Isopropyl (2RS, 3S)-3-{N—{2-(1-naphthylmethyl)-3-[N—methyl-N—(1S—2-bismethoxycarbonylethyl)carbamoyl]propionyl}-L—histidyl}amino-2-hydroxy-5-methylhexanoate | $8.1 \times 10^{-8}$ M |
| Isopropyl (2RS, 3S)-3-{N—{2-(1-naphthylmethyl)-3-[N—methyl-N—(2-hydroxyethyl)carbamoyl]-propionyl}-L—histidyl}amino-2-hydroxy-5-methylhexanoate | $4.1 \times 10^{-8}$ M |
| Isopropyl (2RS, 3S)-3-{N—{2-(1-naphthylmethyl)-3-[bis(2-hydroxyethyl)carbamoyl]propionyl}-1-histidyl}amino-2-hydroxy-5-methylhexanoate | $8.9 \times 10^{-8}$ M |

-continued

| Compound | IC$_{50}$ (molar concentration) |
|---|---|
| Isopropyl (2RS, 3S)-3-{N—[2-(1-naphthylmethyl)-3-(N—methoxy-carbonylmethylcarbamoyl)-propionyl]-1-histidyl}amino-2-hydroxy-5-methylhexanoate | 2.4 × 10$^{-7}$ M |
| Isopropyl (2RS, 3S)-3-{N—[2-(1-naphthylmethyl)-3-(N—methyl-carbamoylmethylcarbamoyl)-propionyl]-L—histidyl}amino-2-hydroxy-5-methylhexanoate | 6.2 × 10$^{-7}$ M |
| Isopropyl (2RS, 3S)-3-{N—{2-(1-naphthylmethyl)-3-[N—(1S—methoxycarbonylethyl)carbamoyl]-propionyl}-L—histidyl}amino-2-hydroxy-5-methylhexanoate | 3.0 × 10$^{-7}$ M |
| Isopropyl (2RS, 3S)-3-{N—{2-(1-naphthylmethyl)-3-[N—(1S—carbamoylethyl)carbamoyl]-propionyl}L—histidyl}amino-2-hydroxy-5-methylhexanoate | 4.4 × 10$^{-7}$ M |
| Methyl (2RS, 3S)-3-{N—[2-(1-naphthylmethyl)-3-(N—methyl-N—methoxycarbonylmethyl-carbamoyl)propionyl]-L—histidyl}amino-2-hydroxy-5-methylhexanoate | 1.2 × 10$^{-8}$ M |
| (2RS, 3S)-3-{N—[2-(1-naphthyl-methyl)-3-(N—methyl-N—methoxy-carbonylmethylcarbamoyl)-propionyl]-L—histidyl}amino-2-hydroxy-5-methylhexanoyliso-amylamide | 2.3 × 10$^{-8}$ M |
| N—[2-(1-naphthylmethyl)-3-(N—methyl-N—methoxycarbonylmethyl-carbamoyl)propionyl[-L—histidyl-statylisoamylamide | 3.5 × 10$^{-8}$ M |
| Isopropyl (2RS, 3S)-3-[3-(methoxycarbonyl)-2-(1-naphthyl-methyl)propionyl-L—histidyl]-amino-2-hydroxy-5-methyl-hexanoate | 2.5 × 10$^{-8}$ M |
| Isopropyl (2RS, 3S)-3-{N—[3-(carbamoyl)-2-(1-naphthyl-methyl)propionyl]-L—histidyl}-amino-2-hydroxy-5-methyl-hexanoate | 5.2 × 10$^{-7}$ M |
| Isopropyl (2RS, 3S)-3-{N—[3-(isopropoxycarbonyl)-2-(1-naphthylmethyl)propionyl]-L—histidyl}amino-2-hydroxy-5-methylhexanoate | 6.4 × 10$^{-8}$ M |
| N—[3-(Methoxylcarbonyl)-2-(1-naphthylmethyl)propionyl]-L—hystidyl-statylisoamylamide | 3.7 × 10$^{-8}$ M |
| (2RS, 3S)-3-[3-Methoxycarbonyl-2-(1-naphthylmethyl)propionyl-L—histidyl]amino-2-hydroxy-5-methylhexanoylisoamylamide | 2.2 × 10$^{-7}$ M |

Test Example 2

Renin inhibitory effect in a human high renin plasma

A mixture of 350 μl of a 0.5M phosphate buffer containing 14 mM EDTA 2Na and a 0.3% neomycin sulfate, which was adjusted to the pH of 7.4, 50 μl of a 20 mM an aqueous solution of L-phenylalanyl-L-alanyl-L-prolin as an angiotensin converting enzyme inhibitor and 100 μl of dimethyl sulfoxide solution containing an amino acid compound of the present invention was added to 500 μl of human high renin plasma. The mixture (800 μl) was incubated for 30 minutes at 37° C. in a water bath. A 200 μl sample was withdrawn from the incubated mixture, chilled immediately in an ice bath, and the amount of angiotensin I produced was determined by radioimmunoassay, and remaining of the mixture (200 μl) was standed at 4° C. in an ice bath.

The amount of angiotensin I produced in the incubated mixture at 4° C. in an ice bath was determined by radioimmunoassay.

As a control, the same procedure as above was carried out by using 100 μl of dimethyl sulfoxide alone in place of the 100 μl of dimethyl sulfoxide solution containing an amino acid compound of the present invention.

The inhibitory effect was calculated by the following equation.

$$\text{Inhibitory effect (\%)} = \frac{\text{Amount of angiotensin I in control} - \text{Amount of angiotensin I in a mixture containing a compound of this invention}}{\text{Amount of angiotensin (I) in control}} \times 100$$

The molar concentration which produced 50% inhibition (IC$_{50}$) was calculated from the inhibition value obtained, and the results are shown below.

| Compound | IC$_{50}$ (molar concentration) |
|---|---|
| Isopropyl (2RS, 3S)-3-{N—[2-1-naphthylmethyl)-3-(2S—methoxycarbonylpyrrolidino-carbonyl)propionyl]-L—histidyl}amino-2-hydroxy-5-methylhexanoate | 5.0 × 10$^{-8}$ M |
| Isopropyl (2RS, 3S)-3-{N—[2-(1-naphthylmethyl)-3-(4-hydroxy-2S—methoxycarbonyl-pyrrolidinocarbonyl)-propionyl]-L—histidyl}amino-2-hydroxy-5-methylhexanoate | 1.9 × 10$^{-7}$ M |
| Methyl (2RS, 3S)-3-{N—[2-(1-naphthylmethyl)-3-(2S—methoxycarbonylpyrrolidino-carbonyl)propionyl]-L—histidyl}amino-2-hydroxy-5-methylhexanoate | 5.3 × 10$^{-8}$ M |
| (2RS, 3S)-3-{N—[2-(1-Naphthyl-methyl)-3-(2S—methoxycarbonyl-pyrrolidinocarbonyl)propionyl]-L—histidyl}amino-2-hydroxy-5-methylhexanoylisoamylamide | 2.9 × 10$^{-7}$ M |
| N—[2-(1-Naphthylmethyl)-3-(2S—methoxycarbonylpyrrolidino-carbonyl)propionyl]-L—histidyl-statylisoamylamide | 2.2 × 10$^{-7}$ M |
| Isopropyl (2RS, 3S)-3-{N—[2-(1-naphthylmethyl)-3-(2S—hydroxy-methylpyrrolidinocarbonyl)-propionyl]-L—histidyl}amino-2-hydroxy-5-methylhexanoate | 1.4 × 10$^{-7}$ M |
| Isopropyl (2RS, 3S)-3-{N—[2-(1-naphthylmethyl)-3-(2R—methoxycarbonylpyrrolidino-carbonyl)propionyl]-L—histidyl}-amino-2-hydroxy-5-methylhexanoate | 1.5 × 10$^{-8}$ M |
| Isopropyl (2RS, 3S)-3-{N—[2-(1-naphthylmethyl)-3-(N—methyl-N—179 N—methoxycarbonylmethylcarbamoyl)-propionyl]-L—histidyl}amino-2-hydroxy-5-methylhexanoate | 2.0 × 10$^{-8}$ M |
| Isopropyl (2RS, 3S)-3-{N—{2-(1-naphthylmethyl)-3-[N—methyl-N—(2-methoxycarbonylethyl)-carbamoyl]propionyl}-L—histidyl}-amino-2-hydroxy-5-methyl-hexanoate | 1.7 × 10$^{-8}$ M |
| Isopropyl (2RS, 3S)-3-{N—{2-(1-naphthylmethyl)-3-[N—methyl- | |

-continued

| Compound | IC$_{50}$ (molar concentration) |
|---|---|
| N—(1S—methoxycarbonylethyl)-carbamoyl]propionyl}-L—histidyl}-amino-2-hydroxy-5-methyl-hexanoate | $1.6 \times 10^{-8}$ M |
| Isopropyl (2RS, 3S)-3-{N—{2-(1-naphthylmethyl)-3-[N—methyl-N—(1S,2-bismethoxycarbonyl-ethyl)carbamoyl]propionyl}-L—histidyl}amino-2-hydroxy-5-methylhexanoate | $1.9 \times 10^{-7}$ M |
| Isopropyl (2RS, 3S)-3-{N—{2-(1-naphthylmethyl)-3-[N—methyl-N—(2-hydroxyethyl)carbamoyl]-propionyl}-L—histidyl}amino-2-hydroxy-5-methylhexanoate | $2.8 \times 10^{-8}$ M |
| Isopropyl (2RS, 3S)-3-{N—{2-(1-naphthylmethyl)-3-[bis(2-hydroxyethyl)carbamoyl]-propionyl}-L—histidyl}amino-2-hydroxy-5-methylhexanoate | $1.8 \times 10^{-7}$ M |
| Isopropyl (2RS, 3S)-3-{N—[2-(1-naphthylmethyl)-3-(N—methoxy-carbonylmethylcarbamoyl)-propionyl]-L—histidyl}amino-2-hydroxy-5-methylhexanoate | $7.6 \times 10^{-8}$ M |
| Isopropyl (2RS, 3S)-3-{N—[2-(1-naphthylmethyl)-3-(N—methyl-carbamoylmethylcarbamoyl)-propionyl]-L—histidyl}amino-2-hydroxy-5-methylhexanoate | $2.9 \times 10^{-7}$ M |
| Isopropyl (2RS, 3S)-3-{N—{2-(1-naphthylmethyl)-3-[N—(1S-methoxycarbonylethyl)carbamoyl]-propionyl}-L—histidyl}amino-2-hydroxy-5-methylhexanoate | $2.1 \times 10^{-7}$ M |
| Isopropyl (2RS, 3S)-3-{N—{2-(1-naphthylmethyl)-3-[N—(1S—carbamoylethyl)carbamoyl]-propionyl}-L—histidyl}amino-2-hydroxy-5-methylhexanoate | $2.4 \times 10^{-7}$ M |
| Methyl (2RS, 3S)-3-{N—[2-(1-naphthylmethyl)-3-(N—methyl-N—methoxycarbonylmethyl-carbamoyl)propionyl]-L—histidyl}amino-2-hydroxy-5-methylhexanoate | $1.4 \times 10^{-8}$ M |
| (2RS, 3S)-3-{N—[2-(1-Naphthyl-methyl)-3-(N—methyl-N—methoxy-carbonylmethylcarbamoyl)-propionyl]-L—histidyl}amino-2-hydroxy-5-methylhexanoyl-isoamylamide | $33.9 \times 10^{-8}$ M |
| N—[2-(1-Naphthylmethyl)-3-(N—methyl-N—methoxycarbonyl-methylcarbamoyl)propionyl]-L—histidyl-statylisoamylamide | $3.5 \times 10^{-8}$ M |
| Isopropyl (2RS, 3S)-3-[3-(methoxycarbonyl)-2-(1-naphthylmethyl)propionyl-L—histidyl]amino-2-hydroxy-5-methylhexanoate | $5.6 \times 10^{-8}$ M |
| Isopropyl (2RS, 3S)-3-{N—[3-(carbamoyl)-2-(1-naphthyl-methyl)propionyl]-L—histidyl}-amino-2-hydroxy-5-methyl-hexanoate | $4.9 \times 10^{-7}$ M |
| Isopropyl (2RS, 3S)-3-{N—[3-(isopropoxycarbonyl)-2-(1-naphthylmethyl)propionyl]-L—histidyl}amino-2-hydroxy-5-methylhexanoate | $1.6 \times 10^{-7}$ M |
| N—[3-(Methoxycarbonyl)-2-(1-naphthylmethyl)propionyl]-L—185 histidyl-statylisoamylamide | $6.0 \times 10^{-8}$ M |
| (2RS, 3S)-3-{N—[3-Methoxy-carbonyl-2-(1-naphthylmethyl)-propionyl]—histidyl}amino-2-hydroxy-5-methylhexanoyl-isoamylamide | $6.9 \times 10^{-7}$ M |

-continued

| Compound | IC$_{50}$ (molar concentration) |
|---|---|
| isoamylamide | |

Test Example 3

Hypotensive effect in marmoset

The experiment was carried out by using common marmoset as described in K. G. Hofbauer et al., *Clinical and Experimental hypertension*, Vol. A5, Nos. 7 & 8 (1983), pages 1237–1247.

Furosemide was orally administered three times to common marmoset at 15 mg per kilogram per day every other day to create a high renin state. Blood pressure of conscious marmoset was measured 2 days after the last administration of furosemide.

Measurement of blood pressure

Two conscious male marmosets weighing 365–380 g were fixed. Mean blood pressure at tail artery was recorded on pretismograph instument. The amino acid compound of the present invention, administered orally using a catheter. The results obtained are shown below.

(a) Compound: Isopropy (2RS, 3S)-3-{N—[2-(1-naphthyl-methyl)-3-(2S—methoxycarbonylpyrrolidino-carbonyl)propionyl]-L—histidyl}amino-2-hydroxy-5-methylhexanoate
Dose: 100 mg/kg (n = 2)

| Time after administration (hours) | Blood pressure (mmHg) |
|---|---|
| control | 94.0 |
| 1 | 77.5 |
| 2 | 74.0 |
| 3 | 70.0 |
| 5 | 92.2 |
| 7 | 101.5 |

(b) Compound: Isopropyl (2RS, 3S)-3-{N—[2-(1-naphthyl-methyl)-3-(N—methyl-N—methoxycarbonyl-methylcarbamoyl)propionyl]-L—histidyl}-amino-2-hydroxy-5-methylhexanoate
Dose: 30 mg/kg (n = 2)

| Time after administration (hours) | Blood pressure (mmHg) |
|---|---|
| Control | 95.4 |
| 1 | 62.1 |
| 2 | 59.8 |
| 3 | 66.5 |
| 5 | 84.9 |
| 7 | 88.3 |

(c) Compound: Isopropyl (2RS, 3S)-3-[3-(methoxycarbonyl)-2-(naphthylmethyl)propionyl-L—histidyl]-amino-2-hydroxy-5-methylhexanoate
Dose: 100 mg/kg (n = 2)

| Time after administration (hours) | Blood pressure (mmHg) |
|---|---|
| Control | 90.9 |
| 1 | 78.6 |
| 2 | 76.9 |
| 3 | 69.4 |
| 5 | 76.0 |
| 7 | 77.8 |
| 9 | 85.3 |

What is claimed is:

1. An amino acid derivative represented by the formula:

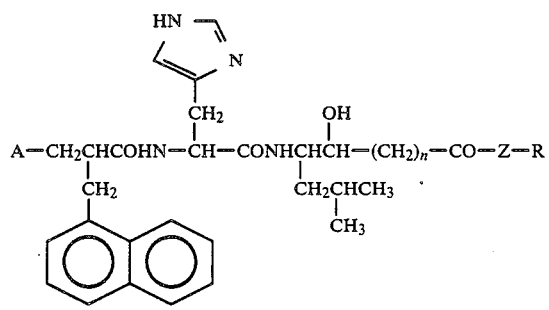 (I)

wherein A represents an alkoxycarbonyl group having 2 to 7 carbon atoms,

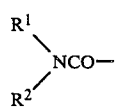

wherein R¹ represents hydrogen atom, an alkyl group having 1 to 6 carbon atoms, a hydroxy alkyl group and R² represents a hydrogen atom or a straight- or branched-chain alkyl group having 1 to 4 carbon atoms with one or two substituents selected from a hydroxy group, an alkoxycarbonyl group having 2 to 7 carbon atoms, a carbamoyl group and an N-alkylcarbamoyl group or

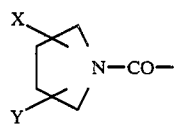

wherein X represents an alkoxycarbonyl group or a hydroxymethyl group and Y represents a hydrogen atom or a hydroxy group, the histidyl structure in formula (I) is an L-histidyl group, n represents zero or one, Z represents —O— or —NH—, and R represents a straight- or branched-chain alkyl group having 1 to 7 carbon atoms, and pharmaceutically acceptable rennin inhibiting acid addition salts thereof.

2. An amino acid derivative as claimed in claim 1 represented by formula:

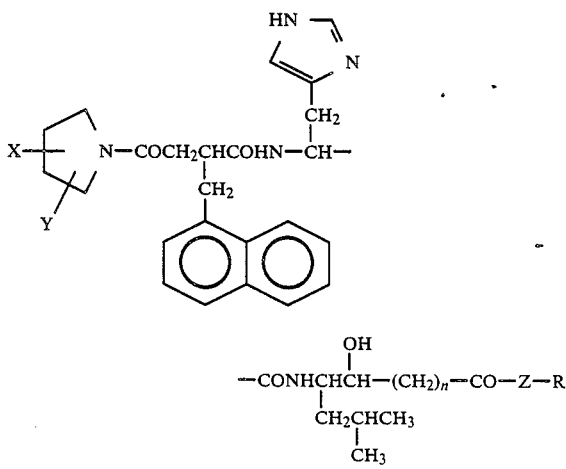

wherein X, Y, n, Z and R have the same meanings as defined above, or a pharmaceutically acceptable renin inhibiting salt thereof.

3. An amino acid derivative as claimed in claim 1 represented by formula:

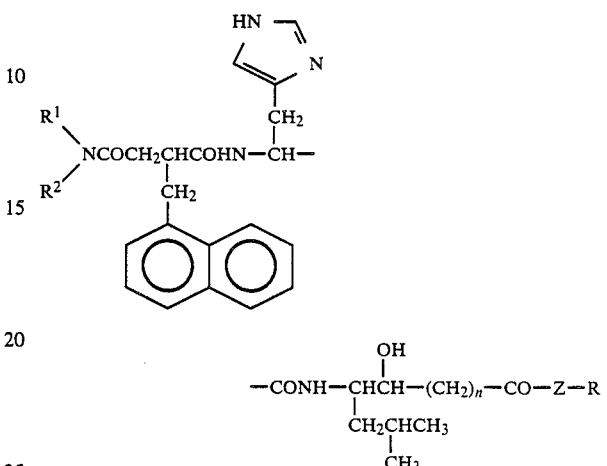

wherein R¹, R², n, Z and R have the same meanings as defined above, or a pharmaceutically acceptable renin inhibiting salt thereof.

4. An amino acid derivative as claimed in claim 1 represented by formula:

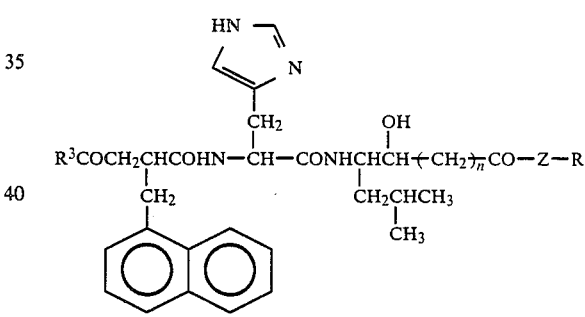

wherein R³ represents an alkoxy group having 1 to 6 carbon atoms, and n, Z and R have the same meanings as defined above, or a pharmaceutically acceptable renin inhibiting salt thereof.

5. The amino acid derivative as claimed in claim 2 represented by formula:

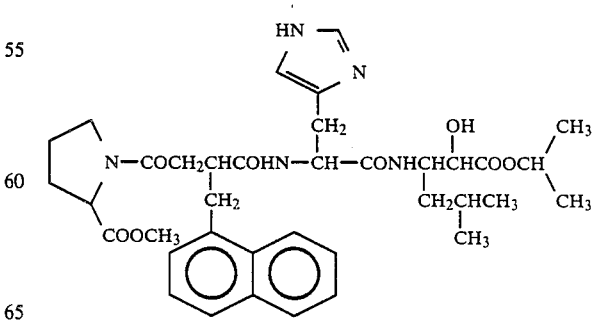

or a pharmaceutically acceptable renin inhibiting salt thereof.

6. The amino acid derivative as claimed in claim 2 represented by the formula:

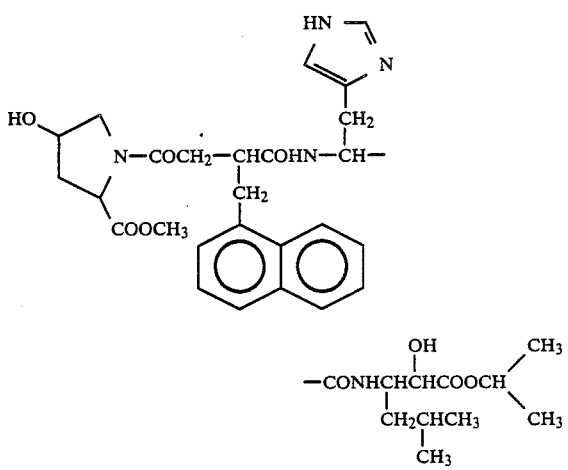

or a pharmaceutically acceptable renin inhibiting salt thereof.

7. The amino acid derivative as claimed in claim 2 represented by the formula

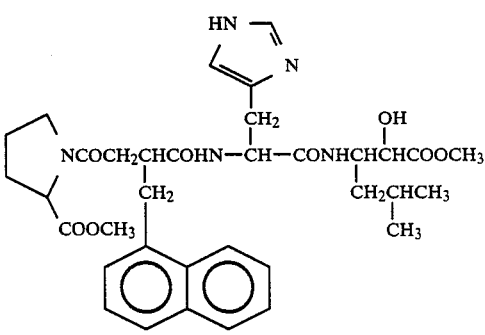

or a pharmaceutically acceptable renin inhibiting salt thereof.

8. The amino acid derivative as claimed in claim 2 represented by formula:

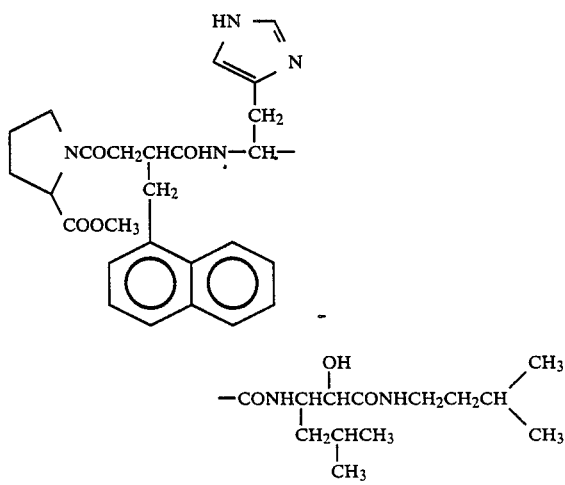

or a pharmaceutically acceptable renin inhibiting salt thereof.

9. The amino acid derivative as claimed in claim 2 represented by formula:

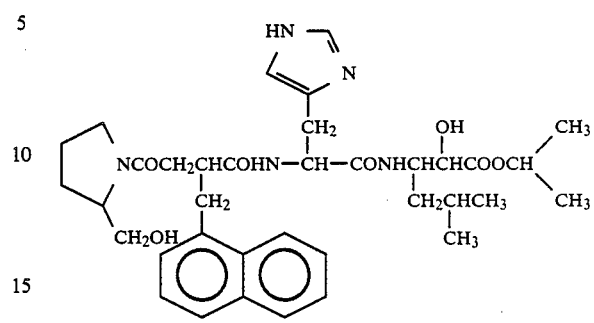

or a pharmaceutically acceptable renin inhibiting salt thereof.

10. The amino acid derivative as claimed in claim 2 represented by formula:

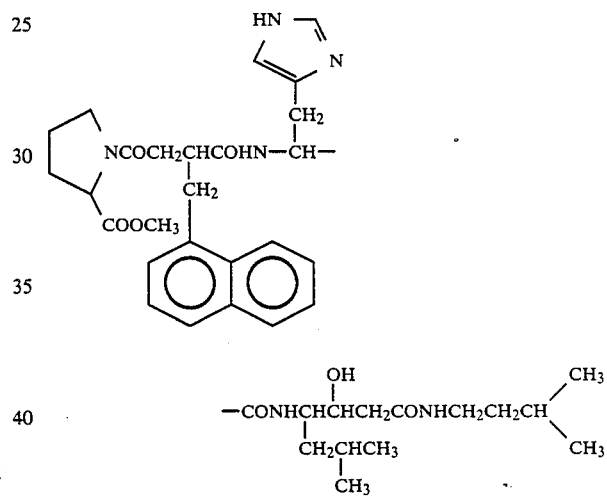

or a pharmaceutically acceptable renin inhibiting salt thereof.

11. The amino acid derivative as claimed in claim 3 represented by formula:

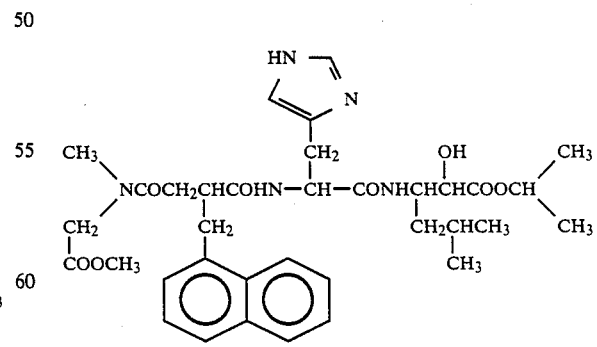

or a pharmaceutically acceptable renin inhibiting salt thereof.

12. The amino acid derivative as claimed in claim 3 represented by formula:

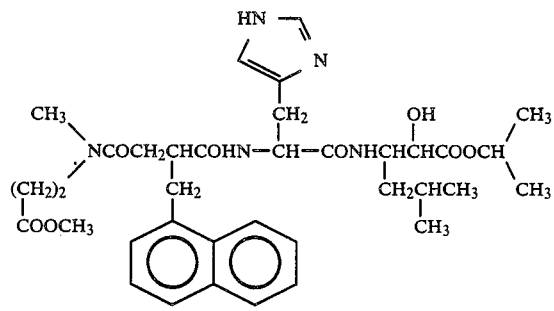

or a pharmaceutically acceptable renin inhibiting salt thereof.

13. The amino acid derivative as claimed in claim 3 represented by formula:

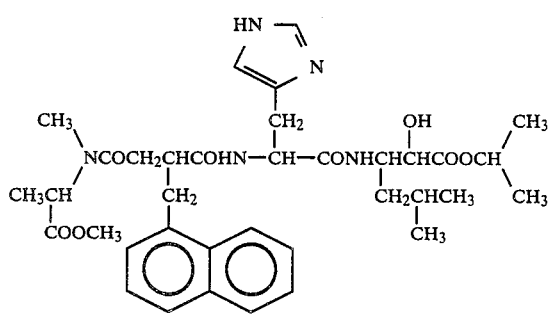

or a pharmaceutically acceptable renin inhibiting salt thereof.

14. The amino acid derivative as claimed in claim 3 represented by formula:

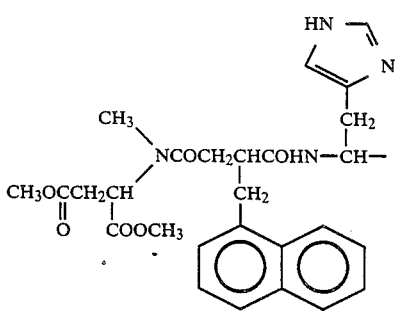

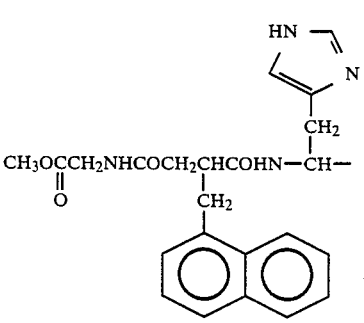

or a pharmaceutically acceptable renin inhibiting salt thereof.

15. The amino acid derivative as claimed in claim 3 represented by formula:

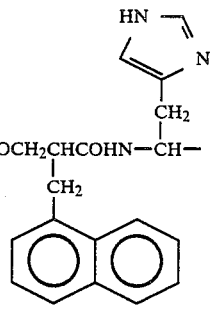

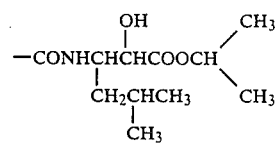

or a pharmaceutically acceptable renin inhibiting salt thereof.

16. The amino acid derivative as claimed in claim 3 represented by formula:

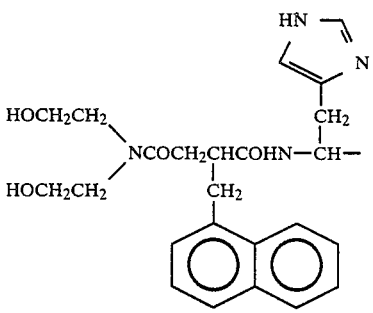

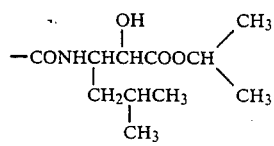

or a pharmaceutically acceptable renin inhibiting salt thereof.

17. The amino acid derivative as claimed in claim 3 represented by formula:

-continued

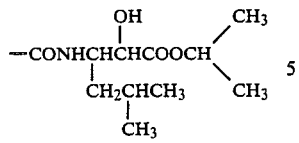

or a pharmaceutically acceptable renin inhibiting salt thereof.

18. The amino acid derivative as claimed in claim 3 represented by formula:

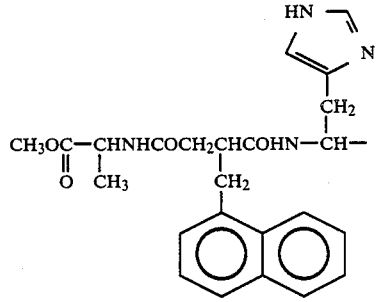

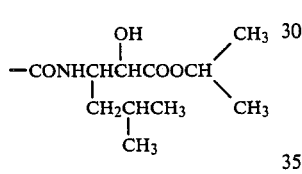

or a pharmaceutically acceptable renin inhibiting salt thereof.

19. The amino acid derivative as claimed in claim 3 represented by formula:

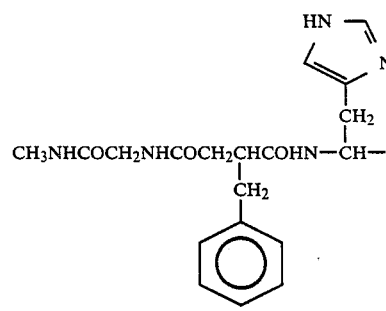

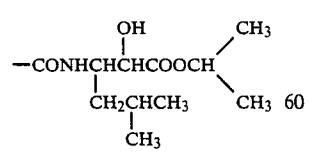

or a pharmaceutically acceptable renin inhibiting salt thereof.

20. The amino acid derivative as claimed in claim 3 represented by formula:

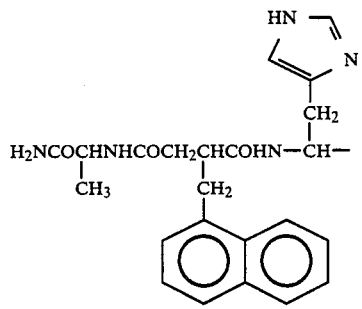

or a pharmaceutically acceptable renin inhibiting salt thereof.

21. The amino acid derivative as claimed in claim 3 represented by formula:

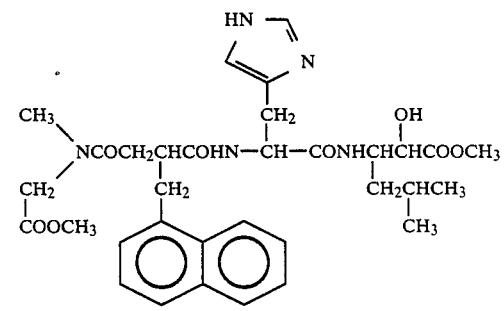

or a pharmaceutically acceptable renin inhibiting salt thereof.

22. The amino acid derivative as claimed in claim 3 represented by formula:

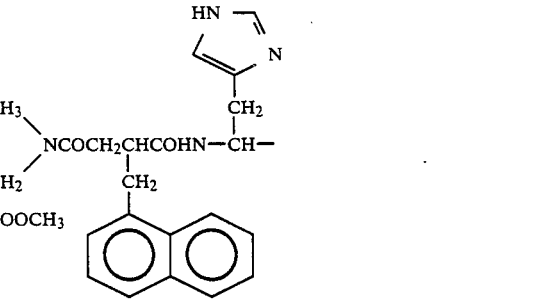

or a pharmaceutically acceptable renin inhibiting salt thereof.

23. The amino acid derivative as claimed in claim 3 represented by formula:

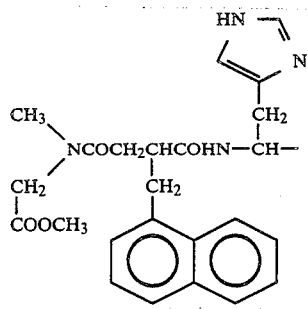

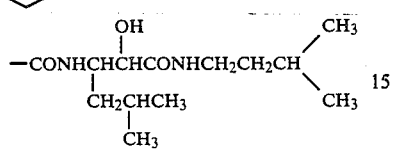

or a pharmaceutically acceptable renin inhibiting salt thereof.

24. The amino acid derivative as claimed in claim 3 represented by formula:

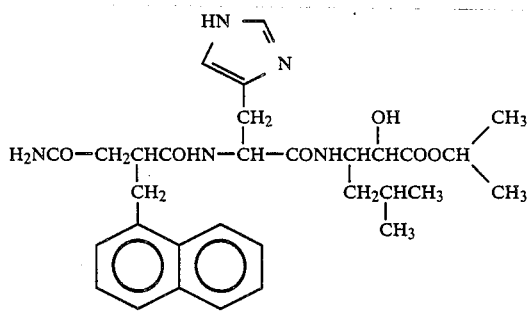

or a pharmaceutically acceptable renin inhibiting salt thereof.

25. The amino acid derivative as claimed in claim 4 represented by formula:

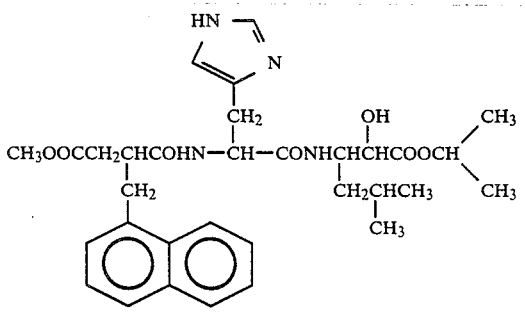

or a pharmaceutically acceptable renin inhibiting salt thereof.

26. The amino acid derivative as claimed in claim 4 represented by formula:

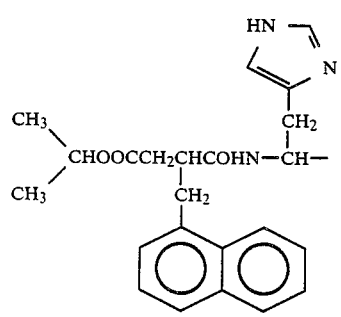

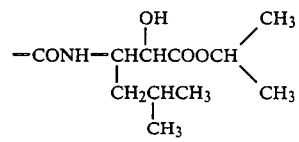

or a pharmaceutically acceptable renin inhibiting salt thereof.

27. The amino acid derivative as claimed in claim 4 represented by formula:

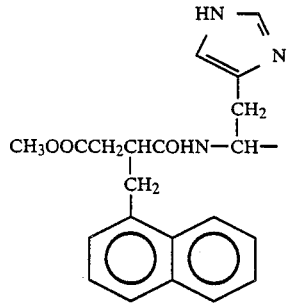

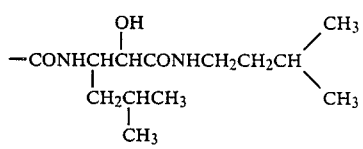

or a pharmaceutically acceptable renin inhibiting salt thereof.

28. The amino acid derivative as claimed in claim 4 represented by formula:

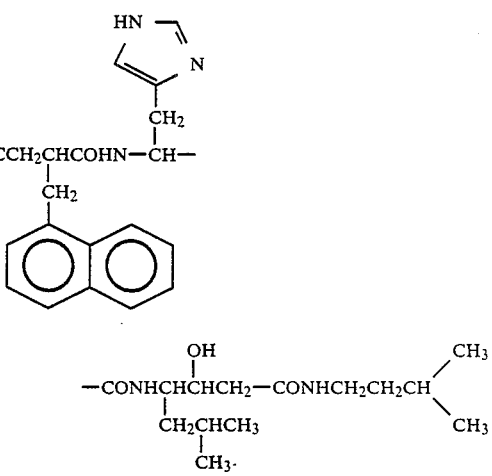

or a pharmaceutically acceptable renin inhibiting salt thereof.

29. The amino acid derivative as claimed in claim 1 wherein said N-alkylcarbamoyl group is an N-methylcarbamoyl group or an N-ethylcarbamoyl group.

30. The amino acid derivative as claimed in claim 2, wherein said N-alkylcarbamoyl group is an N-methylcarbamoyl group or an N-ethylcarbamoyl group.

31. The amino acid derivative as claimed in claim 3, wherein said N-alkylcarbamoyl group is an N-methylcarbamoyl group or an N-ethylcarbamoyl group.

32. The amino acid derivative as claimed in claim 4, wherein said N-alkylcarbamoyl group is an N-methylcarbamoyl group or an N-ethylcarbamoyl group.

* * * * *